United States Patent [19]
Weinshank et al.

[11] Patent Number: 5,935,925
[45] Date of Patent: Aug. 10, 1999

[54] METHODS OF TREATING MIGRAINE AND COMPOUNDS USEFUL FOR SUCH METHODS

[75] Inventors: Richard L. Weinshank, New York, N.Y.; Theresa Branchek, Teaneck; Paul R. Hartig, Mahwah, both of N.J.

[73] Assignee: Synaptic Pharmaceutical Corporation, Paramus, N.J.

[21] Appl. No.: 08/461,812

[22] Filed: Jun. 5, 1995

Related U.S. Application Data

[63] Continuation of application No. 07/946,364, Jan. 8, 1993, abandoned, which is a continuation-in-part of application No. PCT/US91/03200, May 8, 1991, which is a continuation of application No. 07/520,716, May 8, 1990, Pat. No. 5,155,218.

[51] Int. Cl.$^6$ .................................................. A01N 37/18
[52] U.S. Cl. ...................................... 514/2; 514/1; 514/44
[58] Field of Search .............................. 435/69.1; 514/1, 514/2, 44

[56] References Cited

U.S. PATENT DOCUMENTS

| | | | |
|---|---|---|---|
| 4,985,352 | 1/1991 | Julius et al. | 435/6 |
| 5,155,218 | 10/1992 | Weinshank et al. | 536/27 |
| 5,360,735 | 11/1994 | Weinshank et al. | 435/240.2 |
| 5,472,866 | 12/1995 | Gerald et al. | 435/240.2 |
| 5,476,782 | 12/1995 | Weinshank et al. | 435/240.2 |

FOREIGN PATENT DOCUMENTS

| | | |
|---|---|---|
| 1544183 | 12/1983 | Australia . |
| 4568985 | 2/1986 | Australia . |
| 0351921 | 1/1990 | European Pat. Off. . |
| 2124210 | 2/1984 | United Kingdom . |
| 2162522 | 2/1986 | United Kingdom . |
| 8908149 | 9/1989 | WIPO . |
| 9008775 | 8/1990 | WIPO . |

OTHER PUBLICATIONS

Zabel, B.U., et al., Proc. Natl. Acad. Sci. USA 1983 80:6932–6936.
Bethesda Research Laboratories Catalogue and Reference Guide, Life Technologies Inc., 1985, p. 52.
Lubbert, H., et al., Proc. Natl. Acad. Sci. USA 1987 84:4332–4336.
Julius, D., et al., Science 1988 241:558–564.
Fargin, A., et al., Nature 1988 335:358–360.
Libert, F., et al., Science 1989 244:569–572.
Herrick–Davis, K., et al., Synapse 1989 3:325–330.
Libert, F., et al., Nucl. Acids Res. 1990 18:1916.
Albert, P.R., et al. J. Biol. Chem. 1990 265:5825–5832.
Hamblin, M.W.,et al. Biochem. Biophys. Res. Comm. 1992 184:572–579.
Heuring, R.E. , et al., The Journal of Neuroscience 1987. 7(3): 894–903.

(List continued on next page.)

Primary Examiner—Ardin H. Marschel
Attorney, Agent, or Firm—John P. White; Cooper & Dunham LLP

[57] ABSTRACT

This invention provides isolated nucleic acid molecules encoding human 5-HT$_{1D}$ receptors, isolated proteins which are human 5-HT$_{1D}$ receptors, vectors comprising isolated nucleic acid molecules encoding human 5-HT$_{1D}$ receptors, mammalian cells comprising such vectors, antibodies directed to human 5-HT$_{1D}$ receptors, nucleic acid probes useful for detecting nucleic acid encoding human 5-HT$_{1D}$ receptors, antisense oligonucleotides complementary to any sequences of a nucleic acid molecule which encodes a human 5-HT$_{1D}$ receptor, pharmaceutical compounds related to human 5-HT$_{1D}$ receptors, and nonhuman transgenic animals which express DNA which encodes a normal or a mutant human 5-HT$_{1D}$ receptor. This invention further provides methods for determining ligand binding, detecting expression, drug screening, and treatment involving the human 5-HT$_{1D}$ receptor.

8 Claims, 10 Drawing Sheets

OTHER PUBLICATIONS

Kobilka, B.K. et al., Proc. Natl. Acad. Sci. USA 1987 vol. 84, pp. 46–50.
Dohlman, H.G. et al., Biochemistry 1987 26:2664–2668.
Pritchett, D.B., et al., The EMBO Journal vol. 7, No. 13 pp. 4135–4140, 1988.
Waeber, C., et al., Naunyn–Schmiedeberg's Arch Pharmacol 1988, 337: 595–601.
Waeber, C., et al., Neuroscience Letters 88: 11–16, 1988.
Schoeffter, P., et al., Naunyn–Schmiedeberg's Arch Pharmacol 337: 602–608, 1988.
Baar, H.A., et al., Cephalalgia 1989; 9(suppl 9): 83–7.
Doenicke, A., et al., Cephalalgia 1989; 9(suppl 9): 89–92.
Nielsen, T.H., et al., Cephalalgia 1989; 9(suppl 9): 93–5.
Perrin, V.L., et al., Cephalalgia 1989; 9(suppl 9): 63–72.
Peroutka, S.J., et al., European Journal of Pharmacology, 163 pp. 133–136, 1989.
Schmidt, A.W., et al., FASEB J. 3: 2242–2249; 1989.
Schoeffter, P., et al., Naunyn–Schmiedeberg's Arch Pharmacol 340: 285–292; 1989.
Schoeffter, P., et al., Naunyn–Schmiedeberg's Arch Pharmacol 340: 135–138; 1989.
Sumner, M.J., et al., Br. J. Pharmacol. 98: 29–31, 1989.
Xiong, W–C, et al., Life Sci; 45(16) 1433–1442; 1989.
Julius, D., et al., Proc. Natl. Acad. Sci. USA, vol. 87. pp. 928–932, 1990.
Buzzi, G.M., et al., Br. J. Pharmacol. 99: 202–206, 1990.
Branchek, T., et al., Molecular Pharmacology, 38: 604–609, 1990.
Hamel, E., et al., Br. J. Pharmacol. 102: 227–233, 1991.
Zgombick, J.M., et al., Molecular Pharmacology, 40: 1036–1042, 1991.
Branchek, T., et al., Serotonin Molecular Biolohy, Receptors and Functional Effects ed. by J.R. Fozard/P.R. Saxena 1991, pp. 21–32.
Adham, N., et al., Molecular Pharmacology, 41: 1–7, 1991.
Hartig, P.R., et al., TiPS vol. 13 pp. 152–159, 1992.
Weinshank, R.L., et al., Proc, Natl. Acad. Sci. USA vol. 89. pp. 3630–3634, 1992.
Kao, H–T., et al., FEBS vol. 307, No. 3, 324–328, 1992.
Hartig, P.R., Proceedings of the Royal Society of Edinbourgh, 99B(1/2), pp. 19–25, 1992.
Zgombick, J.M., et al., Molecular Pharmacology, 44: 575–582, 1993.
Hamel, E., et al., European Journal of Pharmacology, 242: 75–82, 1993.
Adham, N., et al., Neuropharmaocology vol. 33, No. 3/4, pp. 387–391, 1994.
Chan, R.J., et al., Biochemical and Biophysical Research Communications, vol. 205, No. 2, pp. 1311–1317, 1994.
Zgombick, J.M., et al., European Journal of Pharmacology, Molecular Pharmacology section 291: 9–15, 1995.
Branchek, T.A., et al., Experimental Headache Models, edited by Jes Olesen and Michael A. Mostowitz; pp. 125–134, 1995.

FIG. 3A

```
-280                   -260                   -240
  .         .         .         .         .         .
TGTGGTTTAGGAAAGACCTTTAACTACCAGCTGGTAGTTGTCTCAGCATTCTTCAAATAG
-220                   -200                   -180
  .         .         .         .         .         .
TCCGGTCTTGTTTAATAATATTATTATTGTTATTTAATTTTATTTTATTGCAACTGT
-160                   -140                   -120
  .         .         .         .         .         .
ACTTAGAGAATAGTCTGGTCTTGAGACCTTTTCACTGTGGTCTGTTCTGGTGTACGGCTC
-100                   -80                    -60
  .         .         .         .         .         .
CCACCAGTGTGAAGCAGAAGGATGACTTTGCTCTGTTGTCAGGACAACCTTGAAGGAAGG
-40                    -20                     0
  .         .         .         .         .         .
AGCCAAATGTGTGGAGGTCTGTGGGAAGAGAGAGCCACCTAGCATGTCCCCACTGAACCA
                                             M  S  P  L  N  Q
 20                     40                    60
  .         .         .         .         .         .
GTCAGCAGAAGGCCTTCCCCAGGAGGCCTCCAACAGATCCCTGAATGCCACAGAAACCTC
 S  A  E  G  L  P  Q  E  A  S  N  R  S  L  N  A  T  E  T  S
 80                    100                   120
  .         .         .         .         .         .
AGAGGCTTGGGATCCCAGGACCCTCCAGGCGCTCAAGATCTCCCTTGCCGTGGTCCTTTC
 E  A  W  D  P  R  T  L  Q  A  L  K  I  S  L  A  V  V  L  S
140                    160                   180
  .         .         .         .         .         .
CGTCATCACACTGGCCACAGTCCTCTCCAATGCCTTTGTACTCACCACCATCTTACTCAC
 V  I  T  L  A  T  V  L  S  N  A  F  V  L  T  T  I  L  L  T
200                    220                   240
  .         .         .         .         .         .
CAGGAAGCTCCACACCCCTGCCAACTACCTGATTGGCTCCCTGGCCACCACCGACCTCTT
 R  K  L  H  T  P  A  N  Y  L  I  G  S  L  A  T  T  D  L  L
260                    280                   300
  .         .         .         .         .         .
GGTTTCCATCTTGGTAATGCCCATCAGCATCGCCTATACCATCACCCACACCTGGAACTT
 V  S  I  L  V  M  P  I  S  I  A  Y  T  I  T  H  T  W  N  F
320                    340                   360
  .         .         .         .         .         .
TGGCCAAATCTTGTGTGACATCTGGCTGTCCTCTGACATCACGTGCTGCACAGCCTCCAT
 G  Q  I  L  C  D  I  W  L  S  S  D  I  T  C  C  T  A  S  I
380                    400                   420
  .         .         .         .         .         .
CCTGCATCTCTGTGTCATTGCTCTGGACAGGTACTGGGCAATCACAGATGCCCTGGAATA
 L  H  L  C  V  I  A  L  D  R  Y  W  A  I  T  D  A  L  E  Y
440                    460                   480
  .         .         .         .         .         .
CAGTAAACGCAGGACGGCTGGCCACGCGGCCACCATGATCGCCATTGTCTGGGCCATCTC
 S  K  R  R  T  A  G  H  A  A  T  M  I  A  I  V  W  A  I  S
500                    520                   540
  .         .         .         .         .         .
CATCTGCATCTCCATCCCCCCGCTCTTCTGGCGGCAGGCCAAGGCCCAGGAGGAGATGTC
 I  C  I  S  I  P  P  L  F  W  R  Q  A  K  A  Q  E  E  M  S
```

FIG. 3B

```
560                   580                   600
 .                     .                     .
GGACTGTCTGGTGAACACCTCTCAGATCTCCTACACCATCTACTCCACCTGTGGGCCTT
 D  C  L  V  N  T  S  Q  I  S  Y  T  I  Y  S  T  C  G  A  F
620                   640                   660
 .                     .                     .
CTACATTCCCTCGGTGTTGCTCATCATCCTATATGGCCGGATCTACCGGGCTGCCCGGAA
 Y  I  P  S  V  L  L  I  I  L  Y  G  R  I  Y  R  A  A  R  N
680                   700                   720
 .                     .                     .
CCGCATCCTGAATCCACCCTCACTCTATGGGAAGCGCTTCACCACGGCCCACCTCATCAC
 R  I  L  N  P  P  S  L  Y  G  K  R  F  T  T  A  H  L  I  T
740                   760                   780
 .                     .                     .
AGGCTCTGCCGGGTCCTCGCTCTGCTCGCTCAACTCCAGCCTCCATGAGGGGCACTCGCA
 G  S  A  G  S  S  L  C  S  L  N  S  S  L  H  E  G  H  S  H
800                   820                   840
 .                     .                     .
CTCGGCTGGCTCCCCTCTCTTTTTCAACCACGTGAAAATCAAGCTTGCTGACAGTGCCCT
 S  A  G  S  P  L  F  F  N  H  V  K  I  K  L  A  D  S  A  L
860                   880                   900
 .                     .                     .
GGAACGCAAGAGGATTTCTGCTGCTCGAGAAAGGAAAGCCACTAAAATCCTGGGCATCAT
 E  R  K  R  I  S  A  A  R  E  R  K  A  T  K  I  L  G  I  I
920                   940                   960
 .                     .                     .
TCTGGGGGCCTTTATCATCTGCTGGCTGCCCTTCTTCGTGGTGTCTCTGGTCCTCCCCAT
 L  G  A  F  I  I  C  W  L  P  F  F  V  V  S  L  V  L  P  I
980                   1000                  1020
 .                     .                     .
CTGCCGGGACTCCTGCTGGATCCACCCGGCGCTCTTTGACTTCTTCACCTGGCTAGGCTA
 C  R  D  S  C  W  I  H  P  A  L  F  D  F  F  T  W  L  G  Y
1040                  1060                  1080
 .                     .                     .
TTTAAACTCCCTCATCAATCCAATAATCTACACTGTGTTTAATGAAGAGTTTCGGCAAGC
 L  N  S  L  I  N  P  I  I  Y  T  V  F  N  E  E  F  R  Q  A
1100                  1120                  1140
 .                     .                     .
TTTTCAGAAAATTGTCCCTTTCCGGAAGGCCTCCTAGTCTTATTCGATGAGGTAAAGAAA
 F  Q  K  I  V  P  F  R  K  A  S
1160                  1180                  1200
 .                     .                     .
CCTGCTTATGGGCTGGGCATGGTGGCTCATGCCTGTGATCCCAGCACTTTGGGAAGCTGA
1220                  1240                  1260
 .                     .                     .
AGAGGAGGACTACTTGAGCTCAGGAGTTTGAGACCAGCCTGGGCAGCATAGGGAGACCCC
1280                  1300                  1320
 .                     .                     .
GTCTCTAACGACAACAACAGAAATTACCGGACATGGTGGAGCGCGCCAGTAGTCCCAGCT
1340                  1360
 .                     .
ACTCGAGAGGCTGTGGCTACAGTGA
```

FIG. 4A

```
     0                    -100                  -80
     .                      .                    .
ATTGAGGAACTCACGGAACTATCAACTGGGAACAAACCTGCGATCGCCACGGTCCTTCCG
    -60                   -40                  -20
     .         .            .         .          .         .
CCCTCTCCTTCGTCCGCTCCATGCCCAAGAGCTGCGCTCCGGAGCTGGGGCGAGGAGAGC
     0                     20                   40
     .         .            .         .          .         .
CATGGAGGAACCGGGTGCTCAGTGCGCTCCACCGCCGCCCGCGGGCTCCGAGACCTGGGT
     M  E  E  P  G  A  Q  C  A  P  P  P  P  A  G  S  E  T  W  V
     0                     80                  100
     .         .            .         .          .         .
TCCTCAAGCCAACTTATCCTCTGCTCCCTCCCAAAACTGCAGCGCCAAGGACTACATTTA
  P  Q  A  N  L  S  S  A  P  S  Q  N  C  S  A  K  D  Y  I  Y
    120                    140                  160
     .         .            .         .          .         .
CCAGGACTCCATCTCCCTACCCTGGAAAGTACTGCTGGTTATGCTATTGGCGCTCATCAC
  Q  D  S  I  S  L  P  W  K  V  L  L  V  M  L  L  A  L  I  T
    180                    200                  220
     .         .            .         .          .         .
CTTGGCCACCACGCTCTCCAATGCCTTTGTGATTGCCACAGTGTACCGGACCCGGAAACT
  L  A  T  T  L  S  N  A  F  V  I  A  T  V  Y  R  T  R  K  L
    240                    260                  280
     .         .            .         .          .         .
GCACACCCCGGCTAACTACCTGATCGCCTCTCTGGCAGTCACCGACCTGCTTGTGTCCAT
  H  T  P  A  N  Y  L  I  A  S  L  A  V  T  D  L  L  V  S  I
     0                    320                  340
     .         .            .         .          .         .
CCTGGTGATGCCCATCAGCACCATGTACACTGTCACCGGCCGCTGGACACTGGGCCAGGT
  L  V  M  P  I  S  T  M  Y  T  V  T  G  R  W  T  L  G  Q  V
    360                    380                  400
     .         .            .         .          .         .
GGTCTGTGACTTCTGGCTGTCGTCGGACATCACTTGTTGCACTGCCTCCATCCTGCACCT
  V  C  D  F  W  L  S  S  D  I  T  C  C  T  A  S  I  L  H  L
    420                    440                  460
     .         .            .         .          .         .
CTGTGTCATCGCCCTGGACCGCTACTGGGCCATCACGGACGCCGTGGAGTACTCAGCTAA
  C  V  I  A  L  D  R  Y  W  A  I  T  D  A  V  E  Y  S  A  K
    480                    500                  520
     .         .            .         .          .         .
AAGGACTCCCAAGAGGGCGGCGGTCATGATCGCGCTGGTGTGGGTCTTCTCCATCTCTAT
  R  T  P  K  R  A  A  V  M  I  A  L  V  W  V  F  S  I  S  I
    540                    560                  580
     .         .            .         .          .         .
CTCGCTGCCGCCCTTCTTCTGGCGTCAGGCTAAGGCCGAAGAGGAGGTGTCGGAATGCGT
  S  L  P  P  F  F  W  R  Q  A  K  A  E  E  E  V  S  E  C  V
    600                    620                  640
     .         .            .         .          .         .
GGTGAACACCGACCACATCCTCTACACGGTCTACTCCACGGTGGGTGCTTTCTACTTCCC
  V  N  T  D  H  I  L  Y  T  V  Y  S  T  V  G  A  F  Y  F  P
    660                    680                  700
     .         .            .         .          .         .
CACCCTGCTCCTCATCGCCCTCTATGGCCGCATCTACGTAGAAGCCCGCTCCCGGATTTT
  T  L  L  L  I  A  L  Y  G  R  I  Y  V  E  A  R  S  R  I  L
```

FIG. 4B

```
          720                 740                 760
           .                   .                   .
GAAACAGACGCCCAACAGGACCGGCAAGCGCTTGACCCGAGCCCAGCTGATAACCGACTC
 K  Q  T  P  N  R  T  G  K  R  L  T  R  A  Q  L  I  T  D  S
          780                 800                 820
           .                   .                   .
CCCCGGGTCCACGTCCTCGGTCACCTCTATTAACTCGCGGGTTCCCGACGTGCCCAGCGA
 P  G  S  T  S  S  V  T  S  I  N  S  R  V  P  D  V  P  S  E
          840                 860                 880
           .                   .                   .
ATCCGGATCTCCTGTGTATGTGAACCAAGTCAAAGTGCGAGTCTCCGACGCCCTGCTGGA
 S  G  S  P  V  Y  V  N  Q  V  K  V  R  V  S  D  A  L  L  E
          900                 920                 940
           .                   .                   .
AAAGAAGAAACTCATGGCCGCTAGGGAGCGCAAAGCCACCAAGACCCTAGGGATCATTTT
 K  K  K  L  M  A  A  R  E  R  K  A  T  K  T  L  G  I  I  L
          960                 980                1000
           .                   .                   .
GGGAGCCTTTATTGTGTGTTGGCTACCCTTCTTCATCATCTCCCTAGTGATGCCTATCTG
 G  A  F  I  V  C  W  L  P  F  F  I  I  S  L  V  M  P  I  C
         1020                1040                1060
           .                   .                   .
CAAAGATGCCTGCTGGTTCCACCTAGCCATCTTTGACTTCTTCACATGGCTGGGCTATCT
 K  D  A  C  W  F  H  L  A  I  F  D  F  F  T  W  L  G  Y  L
         1080                1100                1120
           .                   .                   .
CAACTCCCTCATCAACCCCATAATCTATACCATGTCCAATGAGGACTTTAAACAAGCATT
 N  S  L  I  N  P  I  I  Y  T  M  S  N  E  D  F  K  Q  A  F
         1140                1160                1180
           .                   .                   .
CCATAAACTGATACGTTTTAAGTGCACAAGTTGACTTGCCGTTTGCAGTGGGGTCGCCTA
 H  K  L  I  R  F  K  C  T  S
           0                1220                1240
           .                   .                   .
AGCGACCTTTGGGGACCAAGTTGTGTCTGGTTCCACAGGTAGGTCGAATCTTCTTTCGCG
         1260                1280                1300
           .                   .                   .
GTTTCTGGGTCCCAGCGAGGCTCTCTCTCCTGGGCAAGGGCAATGGATCCTGAGAAGCCA
         1320                1340                1360
           .                   .                   .
GAATAGTCCTGAGAGAGAGCTCTGAAAGGAGAAGTGTTGAAACTAAATGTAGAGCTTCCC
         1380                1400                1420
           .                   .                   .
TGCCCAGGAGGAGGCTCACTTCCTCCCCTCAAGCCCCGGGCTCAGCACTGACCTGCGGCA
         1440                1460                1480
           .                   .                   .
GCCAATCCAAGGGGGTTGCAACTTTTAAAAATTGATATGGAAGGGAATCCCTGCCCTGCT
         1500                1520                1540
           .                   .                   .
TTGGTATCGTGATAATGCCCACTAGAAGCAGTGTACTGTAATTGTTGTCTGAAGCCTGTC
         1560
           .
TGAGACAGAT
```

FIG. 6A

```
              1                                                              50
Consensus     M...........  ..sp.nqs.e  gl..eaSn.s  lnatet.eaw  .p.tlqalk.
Pep 8-30-84   M...........  ..SPLNQSAE  GLPQEASNRS  LNATETSEAW  DPRTLQALKI
Pep 11        MEEPGAQCAP    PPPAGSETWV  PQANLSSAPS  QNCSAKDYIY  QDSISLPWKV
RDC4 dog      M...........  ..SPPNQSLE  GLLQEASNRS  LNATETPEAW  GPETLQALKI
5HT1A hum     M...........  ....DVLSPG  QGNNTTSPPA  PFETGGNTTG  ISDVTVSYQV
TM Region     ............  ..........  ..........  ..........  ..........*

51                                                            100
Consensus     sl.lLLs.it   latvlsNafv   l.ti.ltRkL   htpANYLigS   LavTDLlvsi
Pep 8-30-84   SLAVVLSVIT   LATVLSNAFV   LTTILLTRKL   HTPANYLIGS   LATTDLLVSI
Pep 11        LLVMLLALIT   LATTLSNAFV   IATVYRTRKL   HTPANYLIAS   LAVTDLLVSI
RDC4 dog      SLALLLSIIT   MATALSNAFV   LTTIFLTRKL   HTPANYLIGS   LAMTDLLVSI
5HT1A hum     ITSLLLGTLI   FCAVLGNACV   VAAIALERSL   QNVANYLIGS   LAVTDLMVSV
TM Region     .*******.  I..***   *.......   ......**   ***..II 101                                                           150
Consensus     LVmPis.aYt   vt.twt.gQ.   lCDiwlssDi   tCCTaSILHL   CVIALDRYWA
Pep 8-30-84   LVMPISIAYT   ITHTWNFGQI   LCDIWLSSDI   TCCTASILHL   CVIALDRYWA
Pep 11        LVMPISTMYT   VTGRWTLGQV   VCDFWLSSDI   TCCTASILHL   CVIALDRYWA
RDC4 dog      LVMPISIAYT   TTRTWSFGQI   LCDIWLSSDI   TCCTASILHL   CVIALDRYWA
5HT1A hum     LVLPMAALYQ   VLNKWTLGQV   TCDLFIALDV   LCCTSSILHL   CAIALDRYWA
TM Region     .*********   **********   **********   ***..III.    *****.....
```

FIG. 6B

```
              151                                                                          200
Consensus     ITDaleYsk. RT.graAvmI alvWvisicI SiPPlf.WRq akage.msdC
Pep 8-30-84   ITDALEYSKR RTAGHAATMI AIVWAISICI SIPPLF.WRQ AKAQEEMSDC
Pep 11        ITDAVEYSAK RTPKRAAVMI ALVWVFSISI SLPPFF.WRQ AKAEEEVSEC
RDC4 dog      ITDALEYSKR RTAGRAAVMI ATVWVISICI SIPPLF.WRQ AKAQEDMSDC
5HT1A hum     ITDPIDYVNK RTPRPRAL.I SLTWLIGFLI SIPPMLGWRT PEDRSDPDAC
TM Region     ..........  ........*  ******  **..IV..**  **********.

201                                                                          250
Consensus     .vnt..isYT iYSTcGAFYi Ps.LliiLYG RIy.aARnRI l.ppsl..gK
Pep 8-30-84   LVNTSQISYT IYSTCGAFYI PSVLLIILYG RIYRAARNRI LNPPSLY.GK
Pep 11        VVNTDHILYT VYSTVGAFYF PTLLLIALYG RIYVEARSRI LKQTPNRTGK
RDC4 dog      QVNTSQISYT IYSTCGAFYI PSVLLIILYG RIYVAARNRI LNPPSLY.GK
5HT1A hum     TISKDH.GYT IYSTFGAFYI PLLLMLVLYG RIFRAARFRI RKTVKKVE.K
TM Region     ......****  ********  *********.  ......

251                                                                          300
Consensus     rfttaqlitg S.gs..s..s ag.p.ffnhv ..kla..ale
Pep 8-30-84   RFTTAHLITG SAGSSLCSLN SSLHEGHSHS AGSPLFFNHV KIKLADSALE
Pep 11        RLTRAQLITD SPGSTSSVTS INSRVPDVPS ESGSPVYVNQ VKVRVSDALL
RDC4 dog      RFTTAQLITG SAGSSLCSLS PSLQEERSHA AGPPLFFNHV QVKLAEGVLE
5HT1A hum     TGADTRH.GA SPAPQPKKSV NGESGSRNWR LGVESKAGGA LCANGAVRQG
TM Region     ..........  ........  ..........  ..........
```

FIG. 6C

```
                  301                                                           350
Consensus         .k..saa...  ..........  ..........  ..........  ..........
Pep 8-30-84       RKRISAA...  ..........  ..........  ..........  ..........
Pep 11            EKKKLMAA..  ..........  ..........  ..........  ..........
RDC4 dog          RKRISAA...  ..........  ..........  ..........  ..........
5HT$_{1A}$ hum    DDGAALEVIE  VHRVGNSKEH  LPLPSEAGPT  PCAPASFERK  NERNAEAKRK
TM Region         ..........  ..........  ..........  ..........  ..........

351                                                           400
Consensus         ...RERKat   KtLGIilGaF  IvCWLPFF.v  sLVlPiCrds  Cw.hpalfdf
Pep 8-30-84       ....RERKAT  KILGIILGAF  IICWLPFFVV  SLVLPICRDS  CWIHPALFDF
Pep 11            ....RERKAT  INPIIYTVFN  IVCWLPFFII  SLVMPICKDA  CWFHLAIFDF
RDC4 dog          ....RERKAT  KTLGIILGAF  IVCWLPFFVA  SLVLPICRAS  CWLHPALFDF
5HT$_{1A}$ hum    MALARERKTV  KTLGIIMGTF  ILCWLPFFIV  ALVLPFCESS  CHMPTLLGAI
TM Region         ..........  .********   *..VI..***  *******..   .......***

401                           446
Consensus         ftWLGYINSL  iNPiIYtvfN  e.FrqAFqki  ...rkas*.   ..........
Pep 8-30-84       FTWLGYLNSL  INPIIYTVFN  EEFRQAFQKI  VPFRKAS*.   ..........
Pep 11            FTWLGYLNSL  INPIIYTMSN  EDFKQAFHKL  IRFKCTS*.   ..........
RDC4 dog          FTWLGYLNSL  INPIIYTVFN  EEFRQAFQRV  VHVRKAS*.   ..........
5HT$_{1A}$ hum    INWLGYSNSL  LNPVIYAYFN  KDFQNAFKKI  IKCNFCRQ*.  ..........
TM Region         ****..VII.  .********.  ..........  ..........  ..........
```

METHODS OF TREATING MIGRAINE AND COMPOUNDS USEFUL FOR SUCH METHODS

This application is a continuation of U.S. Ser. No. 07/946,364, filed Jan. 8, 1993, now abandoned, which is a continuation-in-part of PCT/US91/03200, filed May 8, 1991, which is a continuation of U.S. Ser. No. 520,716, filed May 8, 1990, now U.S. Pat. No. 5,155,218, the contents of which are incorporated by reference.

BACKGROUND OF THE INVENTION

Throughout this application various publications are referenced by full citations within parentheses. The disclosures of these publications in their entireties are hereby incorporated by reference in this application in order to more fully describe the state of the art to which this invention pertains.

Pharmacological studies, and more recently gene cloning, have established that multiple receptor subtypes exist for most, if not all, neurotransmitters. The existence of multiple receptor subtypes provides one mechanism by which a single neurotransmitter can elicit distinct cellular responses. The variation in cellular response can be achieved by the association of individual receptor subtypes with different G proteins and different signalling systems. Further flexibility is provided by the ability of distinct receptors for the same ligand to activate or inhibit the same second messenger system.

Individual receptor subtypes reveal characteristic differences in their abilities to bind a number of ligands, but the structural basis for the distinct ligand-binding properties is not known. Physiologists and pharmacologists have attempted to specify particular biological functions or anatomical locations for some receptor subtypes, but this has met with limited success. Similarly, the biochemical mechanisms by which these receptors transduce signals across the cell surface have been difficult to ascertain without having well-defined cell populations which express exclusively one receptor subtype.

While all the receptors of the serotonin type recognize serotonin, several pharmacologically distinct subtypes of serotonin receptors have been identified, and given a classification name $5\text{-HT}_X$, where X identifies the subtype. In many cases, these subtypes have been or will be associated with single gene products, but in some cases a single subtype may be found to contain several different receptor proteins (gene products) or two different subtypes may be later shown to arise from different properties of the same receptor protein which are exhibited when it is expressed in different tissue environments. In many cases, different serotonin receptor subtypes have been shown to couple to different second messenger pathways that are linked through guanine-nucleotide regulatory (G) proteins.

Radioligand filtration binding techniques have been employed for over ten years in an effort to more completely characterize receptor subtypes within the serotonin receptor family (Schmidt and Peroutka, FASEB J. 3:2242 (1989)). Using these methods, two broad classes of G protein-coupled serotonin receptors have been described, $5\text{-HT}_1$, and $5\text{-HT}_2$. These differ in their selectivity for drugs. $5\text{-HT}_1$ receptors display high (nanomolar) affinity for serotonin and can be labeled with $[^3\text{H}]5\text{-HT}$. $5\text{-HT}_2$ receptors display low affinity for serotonin but have high (nanomolar) affinity for antagonists such as Ketanserin, Mesulergine, Metergoline and d-LSD.

Within the $5\text{-HT}_1$ receptor class, several subtypes have been distinguished on the basis of their pharmacological binding profiles, second messenger coupling and physiological roles. One such subtype, the $5\text{-HT}_{1D}$ receptor, was originally defined as a particular type of $[^3\text{H}]5\text{-HT}$ binding site in the bovine caudate (Heuring and Peroutka, J. Neurosci. 7:894 (1987)). This definition was not based on properties of a single purified receptor protein or single gene product, but rather was based on experimental observations in a model tissue. As discussed below, later research has shown that there may be multiple receptor proteins (known as subtypes) within this model tissue, all of which contribute to the binding profile that was used to define the $5\text{-HT}_{1D}$ receptor.

The $5\text{-HT}_{1D}$ receptor subtype has been shown to inhibit adenylate cyclase activity (Schoeffter, P. and Hoyer, D., Naunyn-Schmiedeberg's Arch. Pharmacol. 340:285 (1989)). The $5\text{-HT}_{1D}$ receptor subtype has also been characterized in guinea pig (Waeber, et al. Naunyn-Schmiedeberg's Arch. Pharmacol. 340:479–485 (1989)), pigeon (Waeber, 1989), pig (Waeber, et al. Naunyn-Schmiedeberg's Arch. Pharmacol. 377:595–601 (1988)), calf (Waeber, et al. (1988)) and human brain (Waeber, et al. (1988); Herrick-Davis and Titeler, J. Neurochem, 50:1624–1631 (1988)). Among the other serotonin receptor subtypes, the $5\text{-HT}_{1A}$, and $5\text{-HT}_{1B}$ receptors inhibit adenylate cyclase, and $5\text{-HT}_{1C}$ and $5\text{-HT}_2$ receptors activate phospholipase C pathways, stimulating breakdown of polyphosphoinositides (Schmidt and Peroutka, FASEB J. 3:2242 (1989)).

The pharmacological actions of sumatriptan (GR43175), a new anti-migraine medication under development by Glaxo Pharmaceutical Corp., have been linked to the $5\text{-HT}_{1D}$ receptor site (Peroutka and McCarthy, Eur. J. Pharmacology 163:133 (1989)); Schoeffter and Hoyer, Naunyn-Schmiedeberg Arch. Pharmacology 340:135 (1989)). Recently, one report has shown that the $5\text{-HT}_{1D}$ binding site of piglet caudate could be subdivided into two sites, based on the binding affinities of sumatriptan and 5-carboxamidotryptamine (5-CT) (Sumner and Humphrey, Br. J. Pharmacol. 98:29 (1989)). One of these binding sites, with low affinity for sumatriptan and 5-CT, resembles the $5\text{-HT}_{1E}$ site of human cortex (Leonhardt, Herrick-Davis and Titeler, J. Neurochem. 53:465 (1989)) while the binding site with high affinity for these compounds resembles the classic $5\text{-HT}_{1D}$ receptor, and the site of action of sumatriptan.

Another study, by Xiong and Nelson (Life Sci. 45:1433–1442 (1989)) indicated that a high affinity $[^3\text{H}]5\text{-HT}$ binding site in the rabbit caudate, termed the $5\text{-HT}_{1R}$ binding site, is similar to, but pharmacologically distinct from, the $5\text{-HT}_{1D}$ binding site described in the bovine caudate. These authors presented data indicating that two drugs, spiperone and spirilene, exhibited significantly lower affinity for the $5\text{-HT}_{1R}$ binding site than for the $5\text{-HT}_{1D}$ receptor, and noted several other differences in binding properties betweeen these sites. Investigation of the bovine caudate in light of these findings led to the conclusion that there may be a component of the $5\text{-HT}_{1D}$ receptor in bovine caudate that represents a $5\text{-HT}_{1R}$ binding site. Alternatively, the authors speculated that the $5\text{-HT}_{1D}$ binding site in the bovine caudate may be a heterogenous group of sites with similar properties. As noted by the authors, it is clear that additional work will be need to clarify these issues.

A gene for a G protein-coupled receptor was recently isolated by Libert, et al. from a dog cDNA library (Science 244:569–572, 1989). This gene, termed the RDC4 gene, was not expressed by these authors, and therefore no characterization of the properties of the protein encoded by this gene was made. The dog RDC4 gene was isolated and expressed by the applicants, and was determined by the applicants to encode a $5\text{-HT}_{1D}$ receptor (not published).

The serotonin 5-HT$_{1D}$ receptors belong to a family of receptors which are distinguished by their seven-transmembrane configuration and their functional linkage to G-proteins. This family includes rhodopsin and related opsins (Nathans, J. and Hogness, D. S., Cell 34:807 (1983)), the α and β adrenergic receptors (Dohlman, H. G., et al., Biochemistry 26:2657 (1987)), the muscarinic cholinergic receptors (Bonner, T. I., et al., Science 237:527 (1987)), the substance K neuropeptide receptor, (Masu, Y., et al., Nature 329:836 (1987)), the yeast mating factor receptors, (Burkholder, A. C. and Hartwell, L. H., Nucl. Acids Res. 13:8463 (1985); Hagan, D. C., et al., Proc. Natl. Acad. Sci. USA 83:1418 (1986)); Nakayama, N. et al., EMBO J. 4:2643 (1985)), and the oncogene c-mas, (Young, et al., Cell 45:711 (1986)). Each of these receptors is thought to transduce extracellular signals by interaction with guanine nucleotide-binding (G) proteins (Dohluan, H. G., et al., Biochemistry 26:2657 (1987); Dohlman, H. G., et al., Biochemistry 27:1813 (1988); O'Dowd, B. F., et al., Ann. Rev. Neurosci., in press).

SUMMARY OF THE INVENTION

This invention provides an isolated nucleic acid molecule encoding a human 5-HT$_{1D}$ receptor.

This invention also provides an isolated protein which is a human 5-HT$_{1D}$ receptor.

This invention provides a vector comprising an isolated nucleic acid molecule encoding a human 5-HT$_{1D}$ receptor.

This invention also provides vectors such as plasmids comprising a DNA molecule encoding a human 5-HT$_{1D}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding a human 5-HT$_{1D}$ receptor as to permit expression thereof.

This invention provides a mammalian cell comprising a DNA molecule encoding a human 5-HT$_{1D}$ receptor.

This invention provides a method for determining whether a ligand not known to be capable of binding to a human 5-HT$_{1D}$ receptor can bind to a human 5-HT$_{1D}$ receptor which comprises contacting a mammalian cell comprising a DNA molecule encoding a human 5-HT$_{1D}$ receptor with the ligand under conditions permitting binding of ligands known to bind to the 5-HT$_{1D}$ receptor, detecting the presence of any of the ligand bound to the 5-HT$_{1D}$ receptor, and thereby determining whether the ligand binds to the 5-HT$_{1D}$ receptor.

This invention also provides a method of screening drugs to identify drugs which specifically interact with, and bind to, the human 5-HT$_{1D}$ receptor on the surface of a cell which comprises contacting a mammalian cell comprising a DNA molecule encoding a human 5-HT$_{1D}$ receptor on the surface of a cell with a plurality of drugs, determining those drugs which bind to the mammalian cell, and thereby identifying drugs which specifically interact with, and bind to, the human 5-HT$_{1D}$ receptor.

This invention provides a nucleic acid probe comprising a nucleic acid molecule of at least 15 nucleotides capable of specifically hybridizing with a sequence included within the sequence of a nucleic acid molecule encoding a human 5-HT$_{1D}$ receptor.

This invention also provides a method of detecting expression of a 5-HT$_{1D}$ receptor on the surface of a cell by detecting the presence of mRNA coding for a 5-HT$_{1D}$ receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1D}$ receptor under hybridizing conditions, detecting the presence of mRNA hybridized to the probe, and thereby detecting the expression of the 5-HT$_{1D}$ receptor by the cell.

This invention provides an antisense oligonucleotide having a sequence capable of binding specifically with any sequences of an mRNA molecule which encodes a human 5-HT$_{1D}$ receptor so as to prevent translation of the mRNA molecule. This invention provides an antibody directed to the human 5-HT$_{1D}$ receptor.

This invention provides a transgenic nonhuman mammal expressing DNA encoding a human 5-HT$_{1D}$ receptor. This invention also provides a transgenic nonhuman mammal expressing DNA encoding a human 5-HT$_{1D}$ receptor so mutated as to be incapable of normal receptor activity, and not expressing native 5-HT$_{1D}$ receptor. This invention further provides a transgenic nonhuman mammal whose genome comprises antisense DNA complementary to DNA encoding a human 5-HT$_{1D}$ receptor so placed as to be transcribed into antisense mRNA which is complementary to mRNA encoding a 5-HT$_{1D}$ receptor and which hybridizes to mRNA encoding a 5-HT$_{1D}$ receptor thereby reducing its translation.

This invention provides a method of determining the physiological effects of expressing varying levels of human 5-HT$_{1D}$ receptors which comprises producing a transgenic nonhuman animal whose levels of human 5-HT$_{1D}$ receptor expression are varied by use of an inducible promoter which regulates human 5-HT$_{1D}$ receptor expression. This invention also provides a method of determining the physiological effects of expressing varying levels of human 5-HT$_{1D}$ receptors which comprises producing a panel of transgenic nonhuman animals each expressing a different amount of human 5-HT$_{1D}$ receptor.

This invention provides a method for diagnosing a predisposition to a disorder associated with the expression of a specific human 5-HT$_{1D}$ receptor allele which comprises: a. obtaining DNA of subjects suffering from the disorder; b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human 5-HT$_{1D}$ receptor and labelled with a detectable marker; e. detecting labelled bands which have hybridized to the the DNA encoding a human 5-HT$_{1D}$ receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-HT$_{1D}$ receptor allele is diagnosed.

This invention provides a method of preparing the isolated 5-HT$_{1D}$ receptor which comprises inducing cells to express 5-HT$_{1D}$ receptor, recovering the receptor from the resulting cells, and purifying the receptor so recovered. This invention provides a method of preparing the isolated 5-HT$_{1D}$ receptor which comprises inserting nucleic acid encoding 5-HT$_{1D}$ receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention provides a method of determining the physiological effects of expressing varying levels of a receptor which comprises producing a transgenic nonhuman animal whose levels of the receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding a receptor with the ligand under conditions permitting binding of ligands known to bind to a receptor, detecting the presence of any of the ligand bound to the receptor, and thereby determining whether the ligand binds to a receptor.

Two cDNA clones were isolated from a human hippocampus (hH) library by screening approximately 10$^6$ recombinants in a Lambda Zap II vector. Clones hH-13 and hH-46 spanned the entire coding region of gene 5-HT$_{1D-1}$. The seven presumed α-helical membrane-spanning domains (TM-1 to TM-7) are shown and are separated by extracellular (o1–o4) and intracellular (i1–i4) loops.

Figure 2:
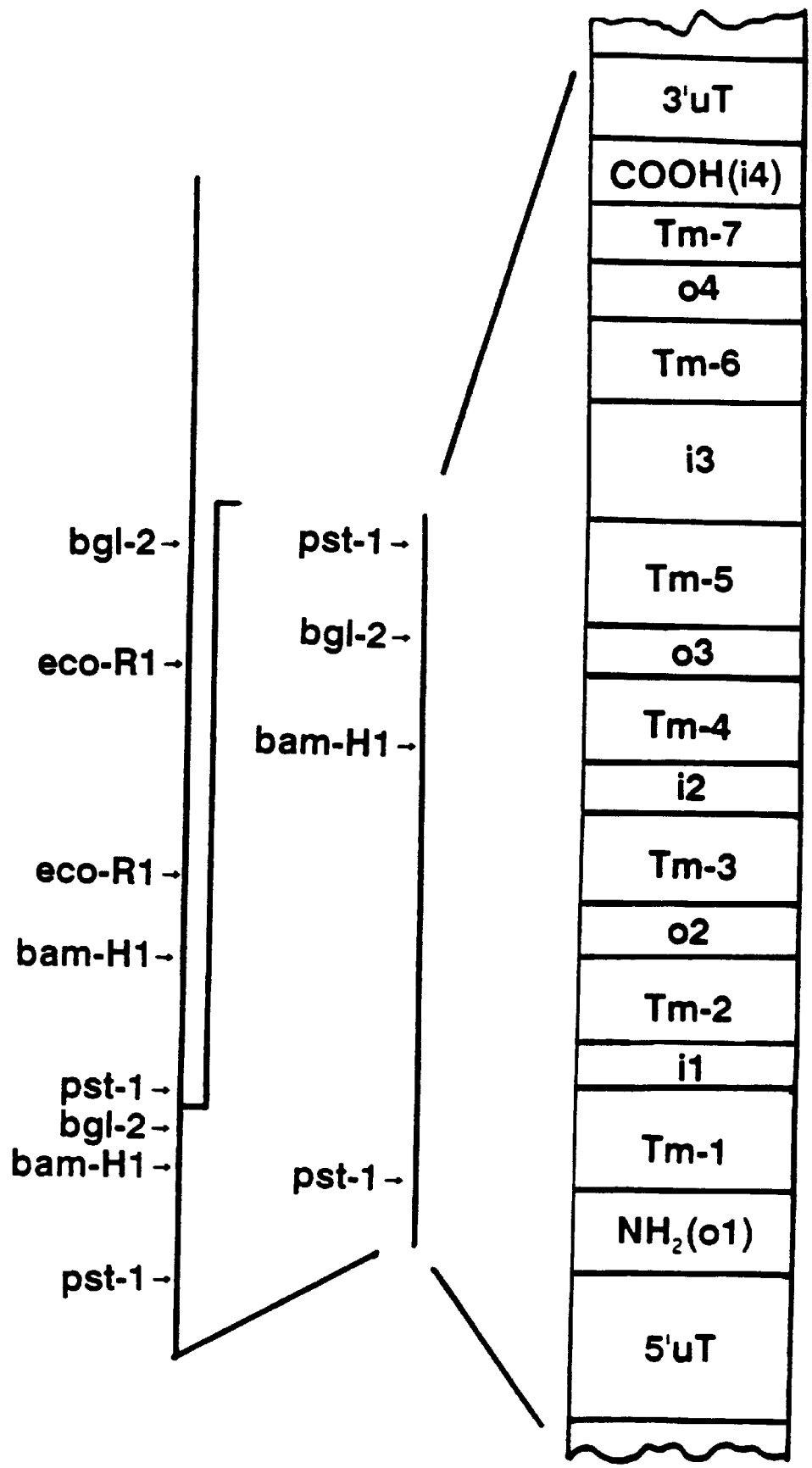

FIG. 2. Restriction map of gene 5-HT$_{1D-2}$ (gene 11). Clone hP-11, containing approximately 15 kilobase (kb) of human genomic DNA was obtained by screening approximately 2 ×10$^6$ recombinants from a Lambda Fix II human placental (hP) genomic library (Stratagene) with the −1.3 kb Hind III-SphI—dog RDC4 probe. The seven presumed α-helical membrane-scanning domains (TM-1 to TM-7) of the deduced amino acid sequence are shown below and are separated by extracellular (o1–o4) and intracellular (i1–i4) loops. Restrictions sites are indicated.

FIGS. 3A and 3B. Nucleotide and deduced amino acid sequence of gene 5-HT$_{1D-1}$ (Sequence I.D. Nos. 1 and 2).

Numbers above the nucleotide sequence indicate nucleotide position. DNA sequence was determined by the chain termination method of Sanger, et al., on denatured double-stranded plasmid templates using the enzyme Sequenase. Deduced amino acid sequence (single letter code) of a long open reading frame is shown. A plasmid comprising the cDNA sequence shown in FIG. 3 has been constructed and is designated pcEXV-8-30-84. The plasmid pcEXV-8-30-84 was deposited on Apr. 17, 1990 pursuant to the provisions of the Budapest Treaty On The International Recognition Of The Deposit Of Microorganisms For The Purposes Of Patent Procedure with the Patent Culture Depository of the American Type Culture Collection (ATCC), 12301 Parklawn Drive, Rockville, Md., 20852, U.S.A. under ATCC Accession No. 40790.

FIGS. 4A and 4B. Nucleotide and deduced amino acid sequence of gene 5-HT$_{1D-2}$ (Sequence I.D. Nos. 3 and 4).

Numbers above the nucleotide sequence indicate nucleotide position. DNA sequence was determined by the chain termination method of Sanger, et al., on denatured double-stranded plasmid templates using the enzyme Sequenase. Deduced amino acid sequence (single letter code) of a long open reading frame is shown. A plasmid comprising the cDNA sequence shown in FIG. 4 has been constructed and is designated pSVL-11. The plasmid pSVL-11 was deposited on Apr. 17, 1990 pursuant to the provisions of the Budapest Treaty On The International Recognition Of The Deposit Of Microorganisms For The Purposes Of Patent Procedure with the Patent Culture Depository of the American Type Culture Collection (ATCC), 12301 Parklawn Drive, Rockville, Md., 20852, U.S.A. under ATCC Accession No. 40791.

Figure 5:
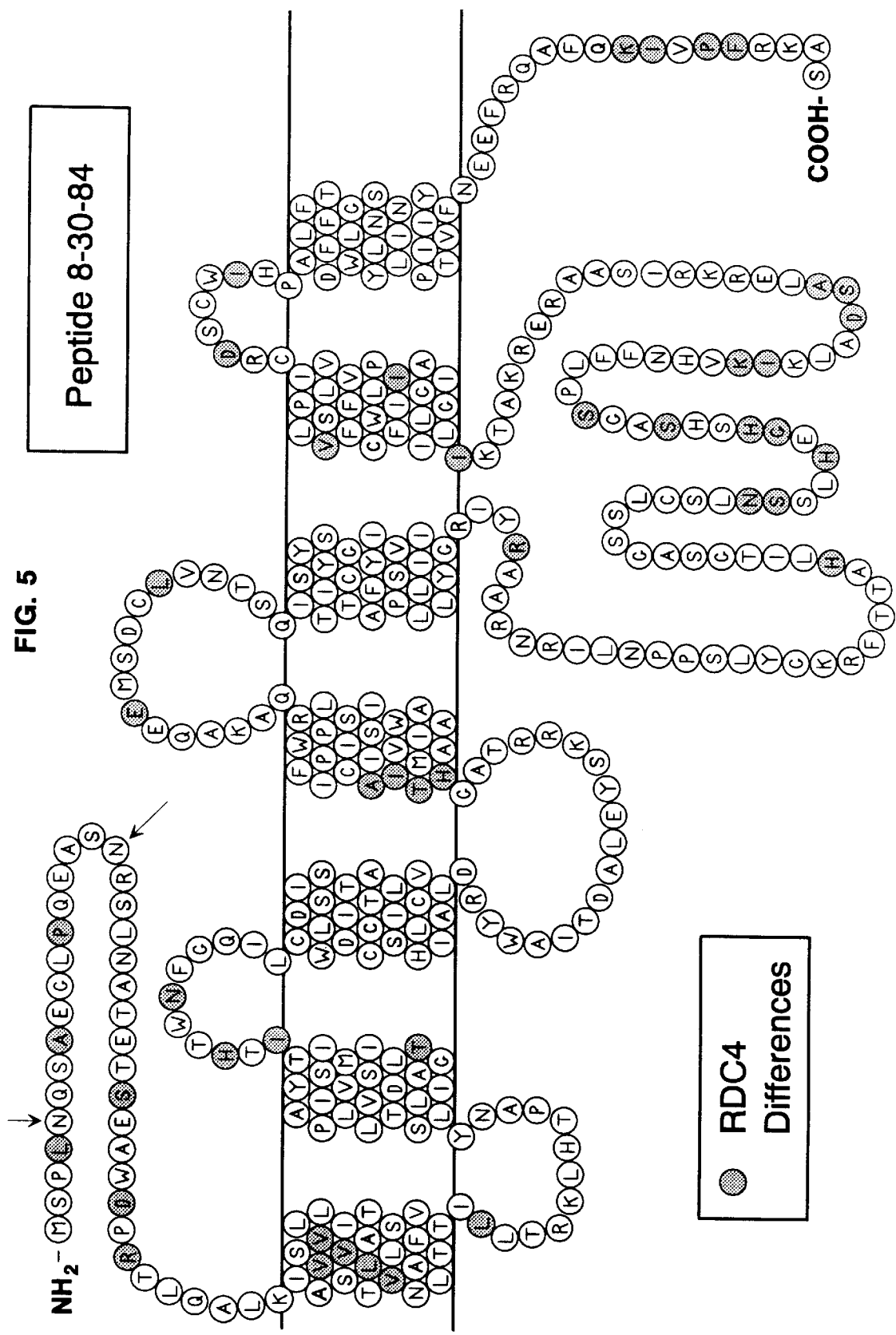

FIG. 5. Seven transmembrane-spanning model of the deduced amino acid sequence of gene 5-HT$_{1D-1}$ (Peptide 8-30-84).

Amino acids in shaded circles are amino acids which differ from the amino acids at the corresponding position in the dog RDC4 receptor. The arrows indicate potential sites of N-linked glycosylation. Amino acids in circles that straddle the lines which represent the membrane are considered outside the transmembrane region for purposes of this application.

FIGS. 6A, 6B and 6C. Comparison of the human 5-HT$_{1D}$ receptor primary structures with other serotonin receptors.

Amino acid sequences (single letter code) are aligned to optimize homology. The putative transmembrane spanning domains are indicated by stars and identified by Roman numerals (TM I–VII).

DETAILED DESCRIPTION OF THE INVENTION

As used herein, the 5-HT receptor family is defined as the group of mammalian proteins that function as receptors for serotonin. A 5-HT receptor subfamily is defined as a subset of proteins belonging to the 5-HT receptor family which are encoded by genes which exhibit homology of 65% or higher with each other in their deduced amino acid sequences within presumed transmembrane regions (linearly contiguous stretches of hydrophobic amino acids, bordered by charged or polar amino acids, that are long enough to form secondary protein structures that span a lipid bilayer). Three human 5-HT receptor subfamilies can be distinguished based on the information presently available. The 5-HT$_2$ receptor subfamily contains the human 5-HT$_2$ receptor. Although no other human members of this family have been described, the rat 5-HT$_2$ receptor (Pritchett, et al. 1988;

Julius, et al. Proc. Natl. Acad. Sci. USA 87:928–932, 1990) and the rat $5HT_{1C}$ receptor (Julius, et al. 1988) constitute a rat 5-HT receptor subfamily. The $5-H_{1A}$ subfamily contains the human $5-HT_{1A}$ receptor, also known as G-21 (Fargin, et al. 1988) The $5-H_{1D}$ receptor subfamily contains two embers, the $5-HT_{1D-1}$ receptor (also termed $5-H_{1Da}$ and/or peptide 8-30-84) and the $5-HT_{1D-2}$ receptor (also termed $5-HT_{1Db}$ and/or peptide 11) which are described herein. Therefore, the term "human $5-HT_{1D}$ receptor" as used herein is defined as meaning a member of the $5-HT_{1D}$ receptor subfamily described above. Although this definition differs from the pharmacological definition used earlier, there is significant overlap between the present definition and the pharmacological definition. Members of the $5-HT_{1D}$ receptor subfamily so described include the $5-HT_{1D-1}$ receptor, the $5-HT_{1D-2}$ receptor, and any other receptors which have a 65% homology to the DNA and amino acid sequence shown in FIGS. 3A and 3B or to the DNA and amino acid sequence shown in FIGS. 4A and 4B, according to the definition of "subfamily". This invention relates to the discovery of the first members of the human $5-HT_{1D}$ receptor subfamily.

This invention provides an isolated nucleic acid molecule encoding a human $5-HT_{1D}$ receptor. Such a receptor is by definition a member of the $5-HT_{1D}$ receptor subfamily. Therefore, any receptor which meets the defining criteria given above is a human $5-HT_{1D}$ receptor. One means of isolating a human $5-HT_{1D}$ receptor is to probe a human genomic library with a natural or artificially designed DNA probe, using methods well known in the art. DNA probes derived from the human receptor genes $5-HT_{1D-1}$ and $5-HT_{1D-2}$ are particularly useful probes for this purpose. DNA and cDNA molecules which encode human $5-HT_{1D}$ receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human $5-HT_{1D}$ receptor. Such molecules may have coding sequences substantially the same as the coding sequence shown in FIGS. 3A and 3B or the coding sequence shown in FIGS. 4A and 4B, or may have coding sequences that are 65% or more homologous to the coding sequence shown in FIGS. 3A and 3B or the coding sequence shown in FIGS. 4A and 4B. The DNA molecules of FIGS. 3A and 3B and FIGS. 4A and 4B encode the sequences of the human $5-HT_{1D}$ receptor genes $5-HT_{1D-1}$ and $5-HT_{1D-2}$.

This invention further provides a cDNA molecule of encoding a human $5-HT_{1D-1}$ receptor having a coding sequence substantially the same as the coding sequence shown in FIGS. 3A and 3B, and a cDNA molecule encoding a human $5-HT_{1D-2}$ receptor having a coding sequence substantially the same as the coding sequence shown in FIGS. 4A and 4B. These molecules are obtained by the means described above.

This invention also provides an isolated protein which is a human $5-HT_{1D}$ receptor. Examples of such proteins are an isolated protein having substantially the same amino acid sequence as the amino acid sequence shown in FIGS. 3A and 3B and an isolated protein having substantially the same amino acid sequence as the amino acid sequence shown in FIGS. 4A and 4B, which are human $5-HT_{1D}$ receptors $5-HT_{1D-1}$ and $5-HT_{1D-2}$. One means for obtaining isolated $5-HT_{1D}$ receptor is to express DNA encoding the receptor in a suitable host, such as a bacterial, yeast, or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human $5-HT_{1D}$ receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. Specific examples of plasmids are a plasmid comprising cDNA having a coding sequence substantially the same as the coding sequence shown in FIGS. 3A and 3B and designated clone p5HT-8-30-84, and a plasmid comprising cDNA having a coding sequence substantially the same as the coding sequence shown in FIGS. 4A and 4B and designated clone p5HT-11.

This invention also provides vectors comprising a DNA molecule encoding a human $5-HT_{1D}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding a human $5-HT_{1D}$ receptor as to permit expression thereof. DNA having coding sequences substantially the same as the coding sequence shown in FIGS. 3A and 3B or the coding sequence shown in FIGS. 4A and 4B may usefully be inserted into the vectors to express human $5-HT_{1D}$ receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, or, in particular, a mammalian cell which comprises a DNA molecule encoding a human $5-HT_{1D}$ receptor and the regulatory elements necessary for expression of the DNA in the bacterial, yeast, or mammalian cell so located relative to the DNA encoding a human $5-HT_{1D}$ receptor as to permit expression thereof.

Some plasmids adapted for expression in a mammalian cell are pSVL (available from Pharmacia, Piscataway, N.J.) and pcEXV-3 (Miller J. and Germain R. N., J. Exp. Med. 164:1478 (1986)). Specific examples of such plasmids are a plasmid adapted for expression in a mammalian cell comprising cDNA having coding sequences substantially the same as the coding sequence shown in FIGS. 3A and 3B and the regulatory elements necessary for expression of the DNA in the mammalian cell which is designated pcEXV-8-30-84 and deposited under ATCC Accession No. 40790, and a plasmid adapted for expression in a mammalian cell comprising cDNA having coding sequences substantially the same as the coding sequence shown in FIGS. 4A and 4B and the regulatory elements necessary for expression of the DNA in the mammalian cell which is designated pSVL-11 and deposited under ATCC Accession No. 40791. Those skilled in the art will readily appreciate that numerous plasmids adapted for expression in a mammalian cell which comprise DNA of encoding human 5-HT$_{1D}$ receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

These deposits discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human 5-HT$_{1D}$ receptor, such as a mammalian cell comprising a plasmid adapted for expression in a mammalian cell, which comprises a DNA molecule encoding a human 5-HT$_{1D}$ receptor and the regulatory elements necessary for expression of the DNA in the mammalian cell so located relative to the DNA encoding a human 5-HT$_{1D}$ receptor as to permit expression thereof. Numerous mammalian cells may be used as hosts, including, for example, the mouse fibroblast cell NIH3T3, CHO cells, HeLa cells, Ltk- cells, etc. A particular example of an Ltk- cell is a cell designated Ltk-8-30-84 and deposited under ATCC Accession No. CRL 10421, and comprises the plasmid designated pcEXV-8-30-84. Another example is a cell designated Ltk-11 and deposited under ATCC Accession No. CRL 10422, and which comprises the plasmid designated pSVL-11. Expression plasmids such as those described supra may be used to transfect mammalian cells by methods well known in the art such as calcium phosphate precipitation, or DNA encoding these 5-HT$_{1D}$ receptors may be otherwise introduced into mammalian cells, e.g., by microinjection, to obtain mammalian cells which comprise DNA, e.g., cDNA or a plasmid, encoding either human 5-HT$_{1D}$ receptor.

This invention provides a method for determining whether a ligand not known to be capable of binding to a human 5-HT$_{1D}$ receptor can bind to a human 5-HT$_{1D}$ receptor which comprises contacting a mammalian cell comprising a DNA molecule encoding a human 5-HT$_{1D}$ receptor with the ligand under conditions permitting binding of ligands known to bind to the 5-HT$_{1D}$ receptor, detecting the presence of any of the ligand bound to the 5-HT$_{1D}$ receptor, and thereby determining whether the ligand binds to the 5-HT$_{1D}$ receptor. The DNA in the cell may have a coding sequence substantially the same as the coding sequence shown in FIGS. 3A and 3B, or the coding sequence shown in FIGS. 4A and 4B. Preferably, the mammalian cell is nonneuronal in origin. An example of a nonneuronal mammalian cell is an Ltk- cell, in particular the Ltk- cell designated L-5HT-8-30-84, or the Ltk- cell designated L-5HT-11. The preferred method for determining whether a ligand is capable of binding to the human 5-HT$_{1D}$ receptors comprises contacting a transfected nonneuronal mammalian cell (i.e. a cell that does not naturally express any type of 5-HT or G-protein coupled receptor, thus will only express such a receptor if it is transfected into the cell) expressing a 5-HT$_{1D}$ receptor on its surface, or contacting a membrane preparation derived from such a transfected cell, with the ligand under conditions which are known to prevail, and thus to be associated with, in vivo binding of the ligands to a 5-HT$_{1D}$ receptor, detecting the presence of any of the ligand being tested bound to the 5-HT$_{1D}$ receptor on the surface of the cell, and thereby determining whether the ligand binds to the 5-HT$_{1D}$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_{1D}$ receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{1D}$ receptor. The transfection system is also useful for determining the affinity and efficacy of known drugs at the human 5-HT$_{1D}$ receptor sites.

This invention also provides a method of screening drugs to identify drugs which specifically interact with, and bind to, the human 5-HT$_{1D}$ receptor on the surface of a cell which comprises contacting a mammalian cell comprising a DNA molecule encoding a human 5-HT$_{1D}$ receptor on the surface of a cell with a plurality of drugs, determining those drugs which bind to the mammalian cell, and thereby identifying drugs which specifically interact with, and bind to, the human 5-HT$_{1D}$ receptor. The DNA in the cell may have a coding sequence substantially the same as the coding sequence shown in FIGS. 3A and 3B, or the coding sequence shown in FIGS. 4A and 4B. Preferably, the mammalian cell is nonneuronal in origin. An example of a nonneuronal mammalian cell is an Ltk- cell, in particular the Ltk- cell designated L-5HT-8-30-84, or the Ltk- cell designated L-5HT-11. Drug candidates are identified by choosing chemical compounds which bind with high affinity to the expressed 5-HT$_{1D}$ receptor protein in transfected cells, using radioligand binding methods well known in the art, examples of which are shown in the binding assays described herein. Drug candidates are also screened for selectivity by identifying compounds which bind with high affinity to one particular 5-HT$_{1D}$ receptor subtype but do not bind with high affinity to any other serotonin receptor subtype or to any other known receptor site. Because selective, high affinity compounds interact primarily with the target 5-HT$_{1D}$ receptor site after administration to the patient, the chances of producing a drug with unwanted side effects are minimized by this approach. This invention provides a pharmaceutical composition comprising a drug identified by the method described above and a pharmaceutically acceptable carrier.

Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a sequence included within the sequence of a nucleic acid molecule encoding a human 5-HT$_{1D}$ receptor, for example with a coding sequence included within the sequence shown in FIGS. 3A and 3B or FIGS. 4A and 4B. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human 5-HT$_{1D}$ receptors is useful as a diagnostic test for any disease process in which levels of expression of the corresponding 5-HT$_{1D}$ receptor is altered. DNA probe molecules are produced by insertion of a DNA molecule which encodes human 5-HT$_{1D}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 3A and 3B and in FIGS. 4A and 4B. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes human 5-HT$_{1D}$ receptor of are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a 5-HT$_{1D}$ receptor on the surface of a cell by detecting the presence of mRNA coding for a 5-HT$_{1D}$ receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1D}$ receptor under hybridizing conditions, detecting the presence of mRNA hybridized to the probe, and thereby detecting the expression of the 5-HT$_{1D}$ receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a human 5-HT$_{1D}$ receptor so as to prevent translation of the mRNA molecule. The antisense oligonucleotide may have a sequence capable of binding specifically with any sequences of the cDNA molecule whose sequence is shown in FIGS. 3A and 3B or the cDNA molecule whose sequence is shown in FIGS. 4A and 4B. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human 5-HT$_{1D}$ receptor by passing through a cell membrane and binding specifically with mRNA encoding a human 5-HT$_{1D}$ receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIGS. 3A and 3B or the coding sequence shown in FIGS. 4A and 4B may be used as the oligonucleotides of the pharmaceutical composition.

This invention also provides a method of treating abnormalities which are alleviated by reduction of expression of a 5-HT$_{1D}$ receptor which comprises administering to a subject an amount of the pharmaceutical composition described above effective to reduce expression of the 5-HT$_{1D}$ receptor by the subject. This invention further provides a method of treating an abnormal condition related to 5-HT$_{1D}$ receptor activity which comprises administering to a subject an amount of the pharmaceutical composition described above effective to reduce expression of the 5-HT$_{1D}$ receptor by the subject. Several examples of such abnormal conditions are dementia, Parkinson's disease, an eating disorder, pathological anxiety, or a migraine headache.

Antisense oligonucleotide drugs inhibit translation of mRNA encoding these receptors. Synthetic oligonucleotides, or other antisense chemical structures are designed to bind to mRNA encoding the 5-HT$_{1D}$ receptor and inhibit translation of mRNA and are useful as drugs to inhibit expression of 5-HT$_{1D}$ receptor genes in patients. This invention provides a means to therapeutically alter levels of expression of human 5-HT$_{1D}$ receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIGS. 3A and 3B or FIGS. 4A and 4B of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequences shown in FIGS. 3A and 3B, and FIGS. 4A and 4B, by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40).

In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of 5-HT$_{1D}$ receptors.

This invention provides an antibody directed to the human 5-HT$_{1D}$ receptor, for example a monoclonal antibody directed to an epitope of a human 5-HT$_{1D}$ receptor present on the surface of a cell and having an amino acid sequence substantially the same as an amino acid sequence for a cell surface epitope of the human 5-HT$_{1D}$ receptor included in the amino acid sequence shown in FIGS. 3A and 3B or included in the amino acid sequence shown in FIGS. 4A and 4B. Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 3A and 3B, or FIGS. 4A and 4B will bind to a surface epitope of a human 5-HT$_{1D}$ receptor, as described. Antibodies directed to human 5-HT$_{1D}$ receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as SR3T3 cells or Ltk- cells may be used as immunogens to raise such an antibody. Alternatively, synthetic peptides may be prepared using commercially available machines and the amino acid sequences shown in FIGS. 3A and 3B and in FIGS. 4A and 4B. As a still further alternative, DNA, such as a cDNA or a fragment thereof, may be cloned and expressed and the resulting polypeptide recovered and used as an immunogen. These antibodies are useful to detect the presence of human 5-HT$_{1D}$ receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human 5-HT$_{1D}$ receptor effective to block binding of naturally occurring ligands to the 5-HT$_{1D}$ receptor, and a pharmaceutically acceptable carrier. A monoclonal antibody directed to an epitope of a human 5-HT$_{1D}$ receptor present on the surface of a cell and having an amino acid sequence substantially the same as an amino acid sequence for a cell surface epitope of the human 5-HT$_{1D}$ receptor included in the amino acid sequence shown in FIGS. 3A and 3B or included in the amino acid sequence shown in FIGS. 4A and 4B are useful for this purpose.

This invention also provides a method of treating abnormalities which are alleviated by reduction of expression of a human 5-HT$_{1D}$ receptor which comprises administering to a subject an amount of the pharmaceutical composition described above effective to block binding of naturally occuring ligands to the 5-HT$_{1D}$ receptor and thereby alleviate abnormalities resulting from overexpression of a human 5-HT$_{1D}$ receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of 5-HT$_{1D}$ receptor activity which comprises administering to a subject an amount of the pharmaceutical composition described above effective to block binding of naturally occurring ligands to the 5-HT$_{1D}$ receptor and thereby alleviate the abnormal condition. Some examples of abnormal conditions are dementia, Parkinson's disease, an eating disorder, a pathological anxiety, and a migraine headache.

This invention provides a method of detecting the presence of a 5-HT$_{1D}$ receptor on the surface of a cell which comprises contacting the cell with an antibody directed to the human 5-HT$_{1D}$ receptor, under conditions permitting binding of the antibody to the receptor, detecting the presence of the antibody bound to the cell, and thereby the presence of the human 5-HT$_{1D}$ receptor on the surface of the cell. Such a method is useful for determining whether a given cell is defective in expression of 5-HT$_{1D}$ receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human 5-HT$_{1D}$ receptor. This invention also provides a transgenic nonhuman mammal expressing DNA encoding a human 5-HT$_{1D}$ receptor so mutated as to be incapable of normal receptor activity, and not expressing native 5-HT$_{1D}$ receptor. This invention also provides a transgenic nonhuman mammal whose genome comprises antisense DNA complementary to DNA encoding a human 5-HT$_{1D}$ receptor so placed as to be transcribed into antisense mRNA which is complementary to mRNA encoding a 5-HT$_{1D}$ receptor and which hybridizes to mRNA encoding a 5-HT$_{1D}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIGS. 3A and 3B, or in the coding sequence shown in FIGS. 4A and 4B. An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of human 5-HT$_{1D}$ receptors are produced by creating transgenic animals in which the expression of a 5-HT$_{1D}$ receptor is either increased or decreased, or the amino acid sequence of the expressed 5-HT$_{1D}$ receptor protein is altered, by a variety of techniques. Examples of these techniques include: 1) Insertion of normal or mutant versions of DNA encoding a human 5-HT$_{1D}$ receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)). 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these 5-HT$_{1D}$ receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human 5-HT$_{1D}$ receptor is purified from a vector (such as plasmid p5HT-8-30-84 or p5HT-11 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these 5-HT$_{1D}$ receptors even before such drugs become available. These animal model systems are useful for predicting or evaluating possible therapeutic applications of drugs which activate or inhibit these 5-HT$_{1D}$ receptors by inducing or inhibiting expression of the native or trans-gene and thus increasing or decreasing expression of normal or mutant 5-HT$_{1D}$ receptors in the living animal. Thus, a model system is produced in which the biological activity of drugs directed against these 5-HT$_{1D}$ receptors are evaluated before such drugs become available. The transgenic animals which over or under produce the 5-HT$_{1D}$ receptor indicate by their physiological state whether over or under production of the 5-HT$_{1D}$ receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to 5-HT$_{1D}$ receptor is indicated as worth developing, and if a promising therapeutic application is uncovered by these animal model systems, activation or inhibition of the 5-HT$_{1D}$ receptor is achieved therapeutically either by producing agonist or antagonist drugs directed against these 5-HT$_{1D}$ receptors or by any method which increases or decreases the expression of these 5-HT$_{1D}$ receptors in man.

This invention provides a method of determining the physiological effects of expressing varying levels of human 5-HT$_{1D}$ receptors which comprises producing a transgenic nonhuman animal whose levels of human 5-HT$_{1D}$ receptor expression are varied by use of an inducible promoter which regulates human 5-HT$_{1D}$ receptor expression. This invention also provides a method of determining the physiological effects of expressing varying levels of human 5-HT$_{1D}$ receptors which comprises producing a panel of transgenic nonhuman animals each expressing a different amount of human 5-HT$_{1D}$ receptor. Such animals may be produced by introducing different amounts of DNA encoding a human 5-HT$_{1D}$ receptor into the oocytes from which the transgenic animals are developed.

This invention also provides a method for identifying a substance capable of alleviating abnormalities resulting from overexpression of a human 5-HT$_{1D}$ receptor comprising administering the substance to a transgenic nonhuman mammal expressing at least one artificially introduced DNA molecule encoding a human 5-HT$_{1D}$ receptor and determining whether the substance alleviates the physical and behavioral abnormalities displayed by the transgenic nonhuman mammal as a result of overexpression of a human 5-HT$_{1D}$ receptor. Examples of DNA molecules are DNA or cDNA molecules having a coding sequence substantially the same as the coding sequence shown in FIGS. 3A and 3B, or the coding sequence shown in FIGS. 4A and 4B.

This invention provides a pharmaceutical composition comprising an amount of the substance described supra effective to alleviate the the abnormalities resulting from overexpression of 5-HT$_{1D}$ receptor and a pharmaceutically acceptable carrier.

This invention further provides a method for treating the abnormalities resulting from overexpression of a human 5-HT$_{1D}$ receptor which comprises administering to a subject an amount of the pharmaceutical composition described above effective to alleviate the abnormalities resulting from overexpression of a human 5-HT$_{1D}$ receptor.

This invention provides a method for identifying a substance capable of alleviating the abnormalities resulting from underexpression of a human 5-HT$_{1D}$ receptor comprising administering the substance to the transgenic nonhuman mammal described above which expresses only nonfunctional human 5-HT$_{1D}$ receptor and determining whether the substance alleviates the physical and behavioral abnormalities displayed by the transgenic nonhuman mammal as a result of underexpression of a human 5-HT$_{1D}$ receptor.

This invention also provides a pharmaceutical composition comprising an amount of a substance effective to alleviate abnormalities resulting from underexpression of a 5-HT$_{1D}$ receptor and a pharmaceutically acceptable carrier.

This invention further provides a method for treating the abnormalities resulting from underexpression of a human 5-HT$_{1D}$ receptor which comprises administering to a subject an amount of the pharmaceutical composition described above effective to alleviate the abnormalities resulting from underexpression of a human 5-HT$_{1D}$ receptor.

This invention provides a method for diagnosing a predisposition to a disorder associated with the expression of a specific human 5-HT$_{1D}$ receptor allele which comprises: a) obtaining DNA of subjects suffering from the disorder; b) performing a restriction digest of the DNA with a panel of restriction enzymes; c. electrophoretically separating the resulting DNA fragments on a sizing gel; d) contacting the resulting gel with a nucleic acid probe capable of specifically hybridizing to DNA encoding a human 5-HT$_{1D}$ receptor and labelled with a detectable marker; e) detecting labelled bands which have hybridized to the DNA encoding a human 5-HT$_{1D}$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-HT$_{1D}$ receptor allele.

This invention provides a method of preparing the isolated 5-HT$_{1D}$ receptor which comprises inducing cells to express 5-HT$_{1D}$ receptor, recovering the receptor from the resulting cells, and purifying the receptor so recovered. An example of an isolated 5-HT$_{1D}$ receptor is an isolated protein having substantially the same amino acid sequence as the amino acid sequence shown in FIGS. 3A and 3B. Another example of an isolated 5-HT$_{1D}$ receptor is an isolated protein having substantially the same amino acid sequence as the amino acid sequence shown in FIGS. 4A and 4B. For example, cells can be induced to express receptors by exposure to substances such as hormones. The cells can then be homogenized and the receptor isolated from the homogenate using an affinity column comprising, for example, serotonin or another substance which is known to bind to the receptor. The resulting fractions can then be purified by contacting them with an ion exchange column, and determining which fraction contains receptor activity or binds anti-receptor antibodies.

This invention provides a method of preparing the isolated 5-HT$_{1D}$ receptor which comprises inserting nucleic acid encoding 5-HT$_{1D}$ receptor in a suitable vector, inserting the resulting vector in a suitable host cell, recovering the receptor produced by the resulting cell, and purifying the receptor so recovered. An example of an isolated 5-HT$_{1D}$ receptor is an isolated protein having substantially the same amino acid sequence as the amino acid sequence shown in FIGS. 3A and 3B. Another example of an isolated 5-HT$_{1D}$ receptor is an isolated protein having substantially the same amino acid sequence as the amino acid sequence shown in FIGS. 4A and 4B. This method for preparing 5-HT$_{1D}$ receptor uses recombinant DNA technology methods well known in the art. For example, isolated nucleic acid encoding 5-HT$_{1D}$ receptor is inserted in a suitable vector, such as an expression vector. A suitable host cell, such as a bacterial cell, or a eucaryotic cell such as a yeast cell, is transfected with the vector. 5-HT$_{1D}$ receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

Applicants have identified individual receptor subtype proteins and have described methods for the identification of pharmacological compounds for therapeutic treatments. Pharmacological compounds which are directed against specific receptor subtypes provide effective new therapies with minimal side effects.

The $5\text{-HT}_{1D}$ receptor subtype was first detected in the caudate nucleus of the bovine brain. It has been widely accepted that $5\text{-HT}_{1D}$ is the non-rodent analog of the $5\text{-HT}_{1E}$ receptor, which has a strong localization in basal ganglia (Schmidt and Peroutka, FASEB J. 3:2242 (1989)). Since the basal ganglia are involved in the control of movement, the $5\text{-HT}_{1D}$ receptor is important in movement control. Additionally, re-examination of previous reports of a $5\text{-HT}_1$ receptor in Parkinson's disease patients, in light of the more recently described $5\text{-HT}_{1D}$ receptor pharmacology, yields an interesting observation. Parkinson's patients with dementia show a large decrease in $5\text{-HT}_1$ receptors in the frontal cortex. (Cross, A. J., Crow, T. J., Johnston, J. A., Perry, E. K., Perry, R. H., Blessed, G. and Tomlinson, B. E., J. Neurol. Sci. 60:383–392, (1989)). This region has recently been shown to contain mainly $5\text{-HT}_{1D}$ receptors within the $5\text{-HT}_1$ class. (Herrick-Davis, K., Titler, M., Leonhardt, S., Struble, R. and Price, D., J. Neurochem. 51:1906–1912 (1988)). These data indicate that $5\text{-HT}_{1D}$ agonists will have significant therapeutic value in ameliorating the dementia of Parkinson's disease, and in treatment of other dementias involving $5\text{-HT}_1$ receptors.

$5\text{-HT}_{1D}$ receptors are implicated in the regulation of feeding behavior, thus providing a treatment for obesity and a potential insight into anorexia and bulimia. In rat models, the $5\text{-HT}_{1D}$ receptor analog $5\text{-HT}_{1B}$ has been implicated in feeding. Agonists of the $5\text{-HT}_{1B}$ receptor such as RU 24924 (but not DPAT) and mCPP both decrease eating (Hutson, P. H., Kennett, G. A., Donohoe, T. P., Dourish, C. T., and Curzon, G. in Behavioral Pharmacology of 5-HT, Bevan, P., Cools, A. R., and Archer, T., eds. Lawrence Erlbaum Associates, Publishers; N.J. (1989) pp. 283–286; Samanin, R. in *Behavioral Pharmacology of 5-HT,* Bevan, P., Cools, A. R., and Archer, T., eds. Lawrence Erlbaum Associates, Publishers; N.J. (1989) pp. 259–283). In other studies, $5\text{-HT}_{1B}$ receptor antagonists cause anorexia (Leander, J. D., in *Behavioral Pharmacology of 5-HT,* Bevan, P., Cools, A. R., and Archer, T., eds. Lawrence Erlbaum Associates, Publishers; N.J. (1989) pp. 287–290). Localization of $5\text{-HT}_{1D}$ receptors in the nucleus accumbens (Samanin, 1989; ibid), part of the neural substrate of feeding behavior, indicate that $5\text{-HT}_{1D}$ agonists have therapeutic value in the control of obesity. Furthermore, $5\text{-HT}_{1D}$ antagonists are useful in reversing endogenous anorexia and in the control of bulimic behavior.

$5\text{-HT}_{1D}$ receptors are also implicated in anxiety. In the rat analog model, $5\text{-HT}_{1B}$ receptor agonists have been reported to decrease the startle response in rats and to effect the defensive burying behavior (Bevan, P., Lorens, S., and Archer, T. in *Behavioral Pharmacology of 5-HT,* Bevan, P., Cools, A. R., and Archer, T., eds. Lawrence Erlbaum Associates, Publishers; N.J. (1989) pp. 459–474). Both paradigms indicate possible therapeutic roles of human $5\text{-HT}_{1D}$ agonists as anxiolytics. Furthermore, yohimbine (a $5\text{-HT}_{1D}$ antagonist) has been shown to worsen panic attacks in man (Charney, D. S., Henenger, G. R., and Breier, A., Arch. Gen. Psychiat. 41:751–763, (1984)).

The best proven therapeutic application of $5\text{-HT}_{1D}$ receptor pharmacology is to migraine treatment. Sumatriptan, an agonist for certain $5\text{-HT}_{1D}$ receptor sites, has been demonstrated to be effective in the control of acute migraine attacks in clinical trials (Doenicke, A., Melchart, D., Bayliss, E. M., Cephalalgia 9 Suppl 9:89–92 (1989)) with few side effects and good efficacy (Baer H. A., Brand, J., Doenicke, A., Melchart, D., Tryba, M., and Sahlender, H. M., Cephalalgia 9 (suppl 9): 83–87, (1989), Perrin, V. L., Farkkila, J., Goasguen, J., Donicke, A., Brand, J., and Tfelt-Hansen, P., Cephalalgia 9(suppl 9) 63–72, (1989)). Sumatriptan appears to be effective against not only the headache but also the nausea, vomiting and sensory disturbances suffered by migraine patients. Applicants have shown (Table 1) that sumatriptan has extremely high affinity at the human $5\text{-HT}_{1D\text{-}1}$ and $5\text{-HT}_{1D\text{-}2}$ receptors.

This invention identifies for the first time two new receptor proteins, their amino acid sequences, and their human genes. Furthermore, this invention describes a previously unrecognized group of receptors within the definition of a $5\text{-HT}_{1D}$ receptor. The information and experimental tools provided by this discovery are useful to generate new therapeutic agents, and new therapeutic or diagnostic assays for these new receptor proteins, their associated mRNA molecules or their associated genomic DNA. The information and experimental tools provided by this discovery will be useful to generate new therapeutic agents, and new therapeutic or diagnostic assays for these new receptor proteins, their associated mRNA molecules, or their associated genomic DNA.

Specifically, this invention relates to the first isolation of human cDNA and genomic clones encoding $5\text{-HT}_{1D}$ receptors. Two new human genes for the receptors identified herein as $5\text{-HT}_{1D\text{-}1}$ and $5\text{-HT}_{1D\text{-}2}$ have been identified and characterized, and a series of related cDNA and genomic clones have been isolated. In addition, the human $5\text{-HT}_{1D}$ receptors have been expressed in Ltk- cells by transfecting the cells with the plasmids pcEXV-8-30-84 and pSVL-11. The pharmacological binding properties of the proteins encoded have been determined, and these binding properties classify these proteins as serotonin $5\text{-HT}_{1D}$ receptors. Mammalian cell lines expressing these human $5\text{-HT}_{1D}$ receptors at the cell surface have ben constructed, thus establishing the first well-defined, cultured cell lines with which to study these $5\text{-HT}_{1D}$ receptors.

The invention will be better understood by reference to the Experimental Details which follow, but those skilled in the art will readily appreciate that the specific experiments detailed are only illustrative of the invention as described more fully in the claims which follow thereafter.

Experimental Details

Isolation of the dog RDC4 gene

The dog RDC4 gene (Libert et al. Science 244:569–572, 1989) was isolated as a prerequisite to isolating clones for human 5-HT$_{1D}$ genes. The RDC4 gene was obtained by isolating clones from a dog genomic library (Stratagene) with an oligonucleotide probe complementary to the large cytoplasmic loop of the RDC4 gene. Overlapping oligomers complementary to the dog RDC4 sequence (GenBank, accession number X14049) were labeled with $^{32}$P-dATP and $^{32}$P-dCTP by synthesis with the large fragment of DNA Polymerase (Maniatis et al. Molecular Cloning, Cold Spring Harbor, 1982). Clones showing positive hybridization to the probe were picked and inserts subcloned into the plasmid pUC-18 (Pharmacia, Piscataway, N.J.). Sequencing via the Sanger dideoxy method confirmed the isolation of a clone containing the entire coding region of the gene.

Isolation of two human 5-HT$_{1D}$ genomic clones

A human placental genomic library (Stratagene) was screened with the 1.3-kilobase (kb) Hind III-Sph I fragment from the dog RDC-4 clone. The probe was labeled with $^{32}$P by the method of random priming (A. P. Feinberg and B. Vogelstein, Anal. Biochem. 137:266 (1984)). Hybridization was performed at 40° C. in a solution containing 50% formamide, 10% dextran sulfate, 5× SSC (1× SSC is 0.15M sodium chloride, 0.015M sodium citrate), 1× Denhardt's (0.02% polyvinyl-pyrrolidone, 0.02% Ficoll, and 0.02% bovine serum albumin), and 200 μg/ml of sonicated salmon sperm DNA. The filters were washed at 50° C. in 0.1× SSC containing 0.1% sodium dodecyl sulfate (SDS) and exposed at −70° C. to Kodak XAR film in the presence of an intensifying screen. Lambda phage hybridizing to the probe were plaque purified and DNA was prepared for Southern Blot analysis (Maniatis et al., Molecular Cloning, Cold Spring Harbor, 1982; E. Southern, J. Mol. Biol. 98:503, 1975). For subcloning and further Southern blot analysis, DNA was inserted into pUC18.

Isolation of cDNA clones

A human hippocampal cDNA library (Stratagene) was screened with an oligonucleotide probe derived from the dog RDC4 sequence (corresponding to amino acid positions number 165 to 188 of the RDC4 sequence in FIGS. 6A, 6B and 6C, which falls within transmembrane region IV). Overlapping oligomers were labeled with $^{32}$P-dATP and $^{32}$P-dCTP as described above (Experimental Details) and the hybridizations and washes were performed as described above for genomic clones (Experimental Details).

DNA Sequencing

Nucleotide sequence analysis was done by the Sanger dideoxy nucleotide chain-termination method (S. Sanger, et al., Proc. Natl. Acad. Sci., 74:5463–5467, 1977) on denatured double-stranded plasmid templates (Chen and Seeburg, DNA 4:165, 1985) using Sequenase (U.S. Biochemical Corp., Cleveland, Ohio).

$^3$H-5HT Binding Assays $^3$H-5HT (20.8-284 Ci/mMol; Dupont, NEN, Wilmington, Del.) was used as a radioligand to detect the expression of the 5-HT gene products in membrane fractions isolated from either transiently or stably transfected cell lines (see Expression). The incubation buffer contained: 50 mM Tris-Cl pH 7.4, 10 mM MgSO$_4$, 0.5 mM EDTA, 1% ascorbic acid and 0.1 mM pargyline. Incubations were initiated by the addition of cell membranes (10–50 μg per well) to 96 well microtiter plates containing $^3$H-5HT (final concentration $10^{-4}$ to $10^{-5}$M) in a final volume of 250 μl. After 15 minutes at 37° C. (in the dark), the incubation was terminated by rapid filtration using a Brandel Cell Harvester (Model 48R; Brandel, Gaithersville, Md.). Specific binding represented 70–80% of total binding, using $10^{-5}$M 5-HT to define nonspecific binding. For competition studies, drugs were initially screened at a concentration of 1–10× their reported K$_i$ values for 5-HT$_{1D}$ receptor binding. Radioactivity trapped on GF/B filter strips was quantitated by liquid scintillation spectroscopy in a Beckman LS5000 TA scintillation counter using Ready Safe liquid scintillation cocktail (Beckman Instruments, Fullerton, Calif.) at an efficiency of 50–55%.

Experimental Results

Isolation of genomic and cDNA clones encoding 5HT1D receptors

Figure 1:
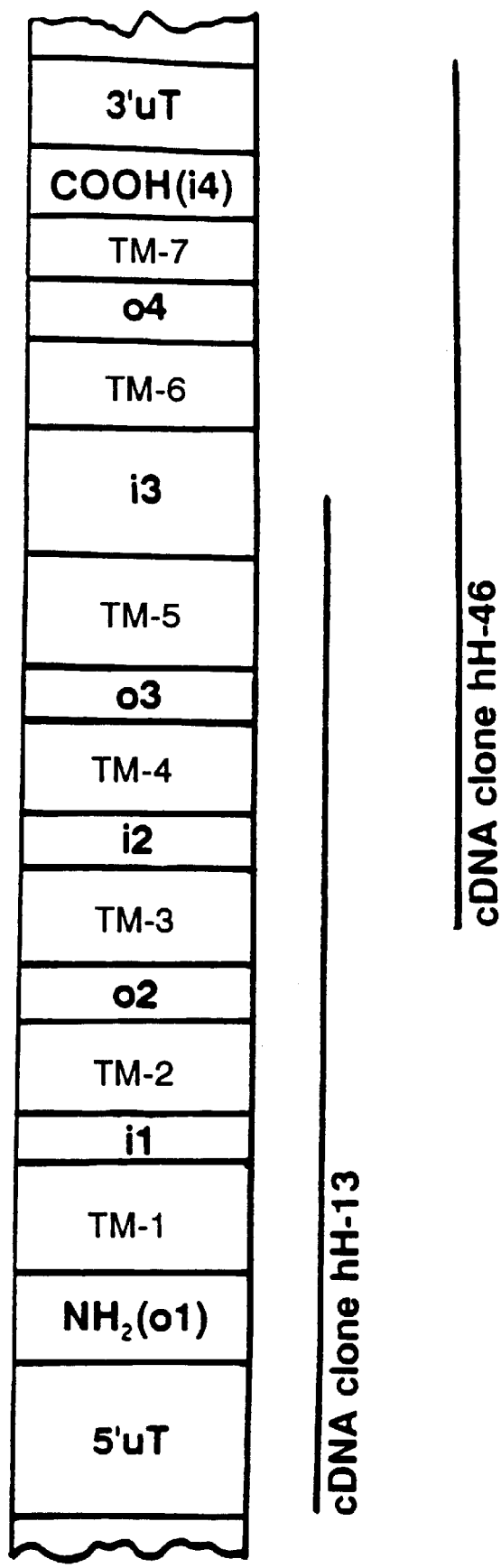
FIG. 1. cDNA clones representing gene 5-HT$_{1D-1}$ (gene 8-30-84).

We have screened a human genomic placental library with the 1.3 kb Hind III-Sph I restriction fragment derived from the dog RDC-4 clone. A total of five human clones were isolated and were characterized by restriction endonuclease mapping and DNA sequence analysis. By restriction analysis all five clones were judged to be different. By sequence analysis two clones, genomic clone hP-8 (human Placenta-8) and genomic clone hP-84, were highly homologous at the nucleotide level (≈90%) to dog RDC4. Following sequence analysis, it was determined that genomic clone hP-8 contained sequence encoding the 5' untranslated (5'UT) region, the amino (NH2) terminus, and transmembrane regions I–III (TM I–III) of a receptor which appears to represent the human homologue of dog RDC4. Genomic clone hP-84 contained sequence corresponding to TM V–VII as well as the carboxy terminus and the 3' UT of this gene. Transmembrane region IV was found to be present on a third clone, genomic clone hP-30. These three genomic clones collectively span the entire coding region of the gene and represent the human version of RDC4. The gene for this new human receptor is designated gene 8-30-84. cDNA clones corresponding to gene 8-30-84 have been isolated from a human hippocampus library (Stratagene) and are designated cDNA clone hH-13 (human Hippocampus-13) and cDNA clone hH-46 (FIG. 1). cDNA clones hH-13 and hH-46 collectively span the entire coding region of this gene.

Two additional genomic clones, clone hP-10 and clone hP-11, were also isolated and characterized. Although both clones were homologous to clone RDC4 at the nucleotide level, their homologies were not as strong (≈75% vs. ≈90% for clones 8 and 84). While genomic clone hP-10 was found to represent a psuedogene of the human RDC4 receptor gene (of gene 8-30-84), genomic clone hP-11 exhibited a genomic structure which appeared to be intronless in the coding region and encodes a gene (gene 11) different from that of gene 8-30-84 (FIG. 2).

Nucleotide sequence and deduced amino acid sequence of gene 8-30-84 (5-HT$_{ID-1}$ gene)

DNA sequence information obtained from gene 8-30-84 is shown in FIGS. 3A and 3B. An open reading frame extending from an ATG start codon at position 1 to a stop codon at position 1131 can encode a protein 376 amino acids in length (peptide 8-30-84), having a relative molecular mass (M$_r$) of 41,783. A compression of this protein sequence with previously characterized neurotransmitter receptors indicates that gene 8-30-84 encodes a receptor which is a new member of a family of molecules which span the lipid bilayer seven times and couple to guanine nucleotide regulatory proteins (the G protein-coupled receptor family). A variety of structural features which are invariant in this family were present in peptide 8-30-84. The greatest homology found was between peptide 8-30-84, the dog RDC-4 receptor and the 5-HT$_{1A}$ receptor. A comparison of peptide 8-30-84 with the dog RDC4 sequence is shown in FIG. 5, which displays a model of the receptor structure organized into seven transmembrane spanning domains. Overall, 87% sequence conservation between the dog RDC4 sequence and the human peptide 8-30-84 was observed over 378 amino acids. The greatest divergence between the dog RDC4 and human gene 8-30-84 protein sequences was seen at the extracellular amino terminus and the large cytoplasmic loop found between TM-V and TM-VI. The homology between these two receptors within the transmembrane regions alone was 92%, with TM-1 being the most divergent.

Nucleotide and deduced amino acid sequence of gene 11 (5-HT$_{1D-2}$ gene)

DNA sequence information obtained from gene 11 is shown in FIGS. 4A and 4B. An open reading frame extending from an ATG codon at position 1 to a stop codon at position 1198 can encode a protein 398 amino acids in length (peptide 11 having a relative molecular mass ($M_r$) of 44,333. A comparison of this protein sequence with previously characterized neurotransmitter receptors indicates that the protein product of gene 11 is also a new member of the G-protein-coupled receptor family. Homology profiles show that the receptor encoded by gene 11 (peptide 11) is tightly related to, but distinct from, the receptor encoded by gene 8-30-84 (peptide 8-30-84) and by the dog RDC4 gene, with the 5HT$_{1A}$ receptor being the next closest receptor with homology to peptide 11 (FIGS. 6A, 6B and 6C). The overall amino acid homology between peptide 8-30-84 and peptide 11 is 56%, with a 76% amino acid homology within the transmembrane regions alone. Virtually no homology exists within the amino terminus, with slight homology found in the large cytoplasmic loop between TM-V and TM-VI as well as the carboxyl terminus. The most divergent of the transmembrane spanning domains is TM-1, which is only 54% identical between peptide 8-30-84 and peptide 11. There doe exist a stretch of four amino acids within TM-1, however, which is identical between peptide 8-30-84 and peptide 11 as well as the dog RDC4 protein product. The sequence of these amino acids is serine(S), and asparagine (N), alanine(A) and phenylalanine(F) and can be abbreviated as "SNAF". This sequence is unique to this subfamily of receptors because it diverges from a conserved sequence (GNxL present in this position of TM-I in a variety of G-protein coupled receptors.

Receptor Expression in Transfected Mammalian Cells

In order to confirm the functional identity of the newly isolated gene we have expressed clones hH-13, hH-46 and hP-11 in cultured cell lines. A DNA fragment containing the entire coding region of the HT$_{1D-1}$ gene, i.e., hH-13 and hH-46, was subcloned into the expression vector pcEXV-3. A DNA fragment containing the entire coding region of the HT$_{1D-2}$ gene, i.e. hP-11, was subcloned into the expression vector pSVL.

Stable cell lines were produced by cotransfection with the plasmid containing the bacterial gene aminoglycoside phosphtransferase into Ltk- cells (American Type Culture Collection, Rockville, Md., Cell Line CCL 1,3) using the calcium phosphate technique (protocol & kit obtained from Specialty Media, Inc. Lavallette, N.J.). Clones expressing aminoglycoside transferase were selected by the addition of 1 mg/ml G418 (Gibco Laboratories, Grand Island, N.Y.) to the culture medium. $^3$H-5HT was used to monitor 5-HT$_{1D}$ receptor gene expression in these clones. Since $^3$H-5HT can also bind to 5-HT$_{1A}$, 5-HT$_{1B}$, and 5-HT$_{1C}$ receptors, the masking ligands pindolol (1 $\mu$M) and SCH 23390 (1 $\mu$M) were included in the incubation.

Cos-7 cells or Ltk- cells were psuedotransfected with vector not containing an insert in order to assess endogenous levels of ligand binding. At 2 nM radioligand, no specific binding was detected. Therefore, Cos-7 and Ltk- cells provide useful models for transfection of a putative 5-HT$_{1D}$ receptor. Transiently transfected Cos-7 cells bound $^3$H-5-HT with high affinity (3 nM) and with an estimated site density of 0.63–1.28 pmole/mg protein for RDC4 and 0.602 to 0.95 pmole/mg protein for peptide 11. The presence of the masking ligands pindolol and SCH 23390 had no significant effect on the specific binding or the pharmacological profile of the detected binding sites in initial studies, and was therefore eliminated in subsequent experiments.

Ltk- cells transfected with RDC4, gene 8 -30-84 or gene 11 bound $^3$H-5-HT with high affinity (K=3.6 nM, 4.0 nM or 2.3 nM, respectively). The estimated B$_{max}$ is equal to 0.275 pm/mg protein for RDC4, 5.1 pmole/mg protein for gene 8-30-84 and 2.3 pmole/mg protein for gene 11. Further characterization was accomplished by performing competition experiments for a series of drugs. Analysis of the competition data was accomplished using the computer-assisted nonlinear regression program Accucomp (Lundon Software; Chagrin Falls, Ohio). Data are shown in Table 1 and indicate that binding detected in the RDC4, gene 8-30-84 or gene 11 transfected cells has properties expected for a 5-HT$_{1D}$ receptor. Additionally, the differences in the affinity of a series of competitors for these two receptors indicates that the RDC4, as well as the human genes, gene 8-30-84 and gene 11, encode proteins with binding properties of a 5-HT$_{1D}$ receptor, and thus uncovers the existence of at least two subtypes of the 5-HT$_{1D}$ receptor.

TABLE 1

[$^3$H]5-HT BINDING TO 5-HT$_{1D}$ RECEPTORS

| DRUG | Cloned Canine 5-HT$_{1D-1}$ (RDC4) | Cloned Human 5-HT$_{1D-1}$ | Cloned Human 5-HT$_{1D-2}$ | Human Native Membranes 5-HT$_{1D}$ |
|---|---|---|---|---|
| Lysergol | N.D. | 0.63 ± 0.10 | 1.2 ± 0.1 | — |
| 5-Carboxamidotryptamine | 0.92 ± 0.06 | 0.70 ± 0.06 | 1.6 ± 0.2 | 0.93[a] |
| Methylergonovine | N.D. | 0.86 ± 0.36 | 2.9 ± 1.5 | — |
| Ergotamine | 1.9 ± 0.3 | 1.0 ± 0.2 | 1.1 ± 0.2 | 0.3[b] |
| CGB-12066B | N.D. | 2.9 ± 0.3 | 2.1 ± 0.3 | — |
| PAPP | 35 ± 6 | 3.1 ± 0.2 | 10 ± 1 | — |
| Sumatriptan | 1.6 ± 0.2 | 3.4 ± 0.3 | 7.7 ± 0.5 | — |
| Methysergide | 7.7 ± 1.7 | 3.6 ± 0.6 | 25 ± 5 | 14[b] |
| 5-Hydroxytryptamine | 5.0 ± 1.4 | 3.9 ± 0.3 | 4.3 ± 0.9 | 6.5[a] |
| 5-methoxy-DMT | 5.1 ± 1.7 | 4.4 ± 0.6 | 21 ± 7 | — |
| 5-Methoxytryptamine | 31 ± 11 | 4.8 ± 0.3 | 34 ± 6 | 6.2[a] |
| Metergoline | N.D. | 5.8 ± 1.1 | 18 ± 3 | 12[a] |
| 1-Napthylpiperazine | N.D. | 7.4 ± 0.6 | 12 ± 2 | — |
| 5-Benzoxytryptamine | N.D. | 9.6 ± 3.0 | 19 ± 8 | — |

TABLE 1-continued

[³H]5-HT BINDING TO 5-HT$_{1D}$ RECEPTORS

| DRUG | Cloned Canine 5-HT$_{1D-1}$ (RDC4) | Cloned Human 5-HT$_{1D-1}$ | Cloned Human 5-HT$_{1D-2}$ | Human Native Membranes 5-HT$_{1D}$ |
|---|---|---|---|---|
| Methiothepin | N.D. | 11 ± 2 | 25 ± 7 | 17[c] |
| Dipropyl-5-CT | N.D. | 13 ± 1 | 42 ± 4 | — |
| Rauwolscine | 5.3 ± 2.9 | 16 ± 2 | 40 ± 7 | — |
| Yohimbine | 32 ± 6 | 22 ± 2 | 27 ± 3 | 42[b] |
| Ritanserin | N.D. | 54 ± 10 | 1200 ± 115 | 3600[c] |
| TFMPP | 112 ± 14 | 64 ± 5 | 114 ± 18 | 210[c] |
| Ketanserin | >1000 | 73 ± 12 | 5198 ± 524 | >10000[b] |
| Tryptamine | 343 ± 15 | 86 ± 6 | 521 ± 32 | 340[b] |
| DPAT | 86 ± 21 | 120 ± 11 | 260 ± 32 | 340[b] |
| NAN-190 | N.D. | 194 ± 12 | 652 ± 48 | — |
| α-methyl-5-HT | N.D. | 211 ± 82 | 133 ± 51 | — |
| mCPP | 429 ± 80 | 216 ± 20 | 361 ± 31 | 1200[c] |
| SCH-23390 | N.D. | 676 ± 69 | 1214 ± 626 | — |
| DOI | 729 ± 102 | 714 ± 81 | 1667 ± 451 | 670[b] |
| Phentolamine | N.D. | 775 ± 72 | 2148 ± 685 | — |
| 2-methyl-5-HT | 444 ± 30 | 915 ± 68 | 860 ± 109 | 1700[c] |
| Spiperone | >1000 | 995 ± 96 | >10000 | >10000[c] |
| Pindolol | >1000 | 4112 ± 504 | 4878 ± 302 | >10000[b] |
| Corynanthine | N.D. | >10000 | >10000 | >10000[c] |
| Zacopride | >10000 | >10000 | >10000 | — |

Estimated equilibrium dissociation constants ($K_i$ values in nM) were calculated from the Cheng-Prusoff relationship for the indicated displacer compounds. Binding experiments were performed on cell membrane preparations from LM (tk-) cells stably transfected with the indicated clones.

[a]Waeber, C., Schoeffter, P., Hoyer, D., and Palacios, J. M. Neurochem. Res., 15:567–582, 1990.
[b]Herrick-Davis, K., Titeler, M., Leonhardt, S., Struble, R., and Price, D. J. Neurochem. 51:1906–1912, 1988.
[c]Peroutka, S. J., Switzer, J. A., and Hamik, A. Synapse, 3:61–66, 1989. N. D., not determined.

Discussion

Applicants have clone and characterized two DNA molecules encoding human 5-HT$_{1D}$ receptors. The expression of these cDNA clones in Cos-7 cells and Ltk- cells results in the appearance of this type of receptor on the cell surface.

The starting point for this research was dog clone RDC4, which was originally reported by Libert et al. (Science 244:569, 1989) as one of a collection of G-protein coupled receptors cloned by PCR technology. Our analysis of the nucleotide sequence following the model of Strader, Sigal and Dixon (FASEB J. 3:1825 (1989)) indicated that RDC4 was likely to be a 5-HT receptor. In addition, RDC4 showed highest sequence homology to the human serotonin 5-HT$_{1A}$ sequence (Libert et al., 1989). The RDC4 sequence was isolated from a dog genomic library in our laboratories, and was transfected into a mammalian cell line. No expression data on this clone have been reported previously by any laboratory.

RDC4-transfected Cos-7 and Ltk- cells were found to bind [³H]5-HT with apparent high affinity ($K_D \approx 3$ nM; Bmax≈0.25–0.4 pm/mg protein). This property indicates that RDC4 encodes a 5-HT$_1$ receptor. High affinity ³H5-HT binding was not affected by co-incubation with (−) pindolol (1 μm). This rules out the possibility that binding is to a 5-HT$_{1A}$ or 5-HT$_{1B}$ receptor. Furthermore, the 5-HT$_{1C}$ antagonist SCH 23390 (1 μm) is also ineffective in reducing the binding of ³H-5-HT. Other compounds unable to compete for ³H-5HT binding sites are ketanserin (5-HT$_2$ receptors), ICS 205–930 (5-HT$_3$ and 5HT$_4$), and 6-OH-indalpine (5-HT$_{1P}$). Furthermore, the high affinity of 5-CT for this binding site rules out the possibility that binding is to a 5-HT$_{1E}$ receptor. The strong sequence homology between RDC4 and this cloned human gene 8-30-84 indicate that the human gene, when transfected into a mammalian cell line, should express very similar pharmacological properties. This has been verified (see Table 1).

RDC4 was also used to clone a second human gene, gene 11. This gene was sequenced and expressed transiently in Cos-7 cells and as a stable cell line in Ltk-. As was shown to be true for the RDC4 clone, gene 11- transfected cells were found to bind ³H-5-HT with high affinity, and to be insensititive to compounds having affinity for 5HT$_{1A}$, 5-HT$_{1B}$, 5-HT$_{1C}$, 5-HT$_3$, or 5-HT$_4$ receptors. Additionally, the ability of low concentrations of 5-CT to compete with [³H]5-HT for binding to gene 11-transfected cells excludes the possibility that this gene encodes a 5-HT$_{1P}$ or 5-HT$_{1E}$ receptor. The pharmacological profile is shown in Table 1. These data are consistent with the characterization of gene 11 as encoding a 5HT$_{1D}$ receptor.

Table 1 demonstrates that although RDC4 (and peptide 8-30-84) and peptide 11 can both be classified as 5-HT$_{1D}$ receptors, they have distinct pharmacological differences as well as distinct structures. These data demonstrate for the first time that the human 5-HT$_{1D}$ binding site constitutes not a single receptor but a family of receptors. Potential differences in localization as well as pharmacology may be exploited in the future to develop powerful new drugs for selectively activating or inhibiting each of these 5-HT$_{1D}$ receptor sites.

In summary, we have cloned two human 5-HT$_{1D}$ receptors with differing pharmacological properties. This indicates that 5-HT$_{1D}$ receptors constitute a receptor family rather than a single protein. In human brain, 5-HT$_{1D}$ receptors have been shown to have the strongest representation in frontal cortex, putamen, caudate, both parts of the globus pallidus and the substantia nigra. Lower amounts are found in the raphe nuclei, hippocampus, and accumbens. 5-HT$_{1D}$ receptors have been implicated in a number of clinically important conditions including migraine, appetite, movement control, anxiety, and dementia. 5-HT$_{1D}$ agonists such as sumatriptan, are now in clinical trials. Our data, showing that there are multiple subtypes of human 5-HT$_{1D}$ receptors, opens a new avenue for drug discovery. Pharmacological differences in these 5-HT$_{1D}$ receptor subtypes, coupled with our exploration of possible differences in their localization, will likely lead to the development of more selective therapeutic agents with differential sensitivity for these subtypes.

Additional Experimental Data Relating to Pharmacological Characterization of a Cloned Rat 5-HT$_{1B}$ Receptor: Relationship to the Cloned 5-HT$_{1D}$ Receptor The 5-HT$_{1B}$ and 5-HT$_{1D}$ receptors display similarities in their pharmacology, second messenger coupling, and anatomical distribution. This close relationship has led to the proposal that these receptors are species homologs, whereby the rat and mouse (and opossum) express the 5-HT$_{1B}$ receptor and other species such as human, dog, bovine and guinea pig express the 5-HT$_{1D}$ receptor (Hoyer and Middlemiss, 1989). The recent cloning of a 5-HT$_{1D}$ receptor (Branchek et al., 1990) has allowed access to a direct assessment of the relationship between these two receptors using molecular cloning techniques. The isolate the putative rat homolog of the 5-HT$_{1D}$ gene, a rat library was screened at high stringency using a human 5-HT$_{1D}$ sequence as a probe. A strongly hybridizing signal was selected for study, subcloned, and transiently transfected into a mammalian cell line (Cos-7). To identify the pharmacological profile of this receptor, radioligand binding assays were performed on a membrane fraction derived from the transfected cells. [$^3$H] 5-HT and [$^{125}$I]iodocyanopindolol ([$^{125}$I]I-CYP in the presence of 3 $\mu$M isoproterenol to block endogenous $\beta$-adrenergic receptors) were used as radioligands. [$^{125}$I] iodocyanopindolol was found to bind the membranes derived from the transfected cells with subnanomolar affinity [K$_d$=0.16 nM]. In contrast, the equilibrium dissociation constant for [$^3$H]5-HT binding was 18.4 nM. These values were in marked contrast to those measured using the human 5-HT$_{1D}$ clone ([$^3$H]5-HT: K$_d$=4 nM; [$^{125}$I]I-CYP: no specific binding detected at 1 nM). The rauwolfia alkaloid rauwolscine was essentially inactive (K$_i$>10,000 nM) at the rat receptor as was dipropyl-5-carboxyamidotryptamine. The rank order of potencies for the compounds studied as 5-HT>(-) propranolol>5 methoxytryptamine>tryptamine>dipropyl-5-carboxyaminotryptamine=rauwolscine. These data clearly indicate that the gene isolated by homology with the human 5-HT$_{1D}$ receptor encodes a protein with pharmacological properties which identify it as a 5-HT$_{1D}$ receptor. Therefore, it appears that these receptors are species homologs which exhibit significant differences in pharmacology. A similar situation has been descrived for the rat and human 5-HT$_2$ receptors which have been cloned previously and shown to be highly homologous (Hartig et al., 1990). However, the differences in the pharmacological properties of the 5-HT$_{1B}$/5-HT$_{1D}$ receptors have been shown to be more robust than those of the rat 5-HT$_2$/human 5-HT$_2$ receptors.

What is claimed is:

1. A method of treating migraine in a subject which comprises administering to the subject a chemical compound which selectively binds to and activates a human 5-HT$_{1D}$ receptor but not a 5-HT$_{1A}$ receptor, a 5-HT$_{1E}$ receptor, a 5-HT2 receptor, a 5-HT$_3$ receptor, or a 5-HT$_4$ receptor, wherein the human 5-HT$_{1D}$ receptor is selected from the group consisting of the human 5-HT$_{1D-1}$ receptor and the human 5-HT$_{1D-2}$ receptor, so as to treat the subject's migraine with the proviso that the compound is not methylergonovine, ergotamine, sumatriptan or pindolol.

2. A method of treating migraine in a subject which comprises administering to the subject a chemical compound which selectively binds to and activates a human 5-HT$_{1D}$ receptor but not any other serotonin receptor, wherein the human 5-HT$_{1D}$ receptor is selected from the group consisting of the human 5-HT$_{1D-1}$ receptor and the human 5-HT$_{1D-2}$ receptor, so as to treat the subject's migraine with the proviso that the compound is not methylergonovine, ergotamine, sumatriptan or pindolol.

3. A pharmaceutical composition for treating migraine in a subject which comprises an acceptable carrier and an amount of a chemical compound which selectively binds to and activates a human 5-HT$_{1D}$ receptor but not a 5-HT$_{1A}$ receptor, a 5-HT$_{1E}$ receptor, a 5-HT$_2$ receptor, a 5-HT$_3$ receptor, or a 5-HT$_4$ receptor effective to treat the subject's migraine, wherein the human 5-HT$_{1D}$ receptor is selected from the group consisting of the human 5-HT$_{1D-1}$ receptor and the human 5-HT$_{1D-2}$ receptor, with the provision that the compound is not methylergonovine, ergotamine, sumatriptan or pindolol.

4. A pharmaceutical composition for treating migraine in a subject which comprises an acceptable carrier and an amount of a chemical compound which selectively binds to and activates a human 5-HT$_{1D}$ receptor but not any other serotonin receptor effective to treat the subject's migraine, wherein the human 5-HT$_{1D}$ receptor is selected from the group consisting of the human 5-HT$_{1D-1}$ receptor and the human 5-HT$_{1D-2}$ receptor, with the proviso that the compound is not methylergonovine, ergotamine, sumatriptan or pindolol.

5. A method of treating migraine in a subject which comprises administering to the subject a chemical compound which selectively binds to and activates a human 5-HT$_{1D}$ receptor but not a 5-HT$_{1A}$ receptor, a 5-HT$_{1E}$ receptor, a 5-HT$_2$ receptor, a 5-HT$_3$ receptor, or a 5-HT$_4$ receptor, wherein the human 5-HT$_{1D}$ receptor is a human 5-HT$_{1D-1}$ receptor and a human 5-HT$_{1D-2}$ receptor, so as to treat the subject's migraine with the proviso that the compound is not methylergonovine, ergotamine, sumatriptan or pindolol.

6. A method of treating migraine in a subject which comprises administering to the subject a chemical compound which selectively binds to and activates a human 5-HT$_{1D}$ receptor but not any other serotonin receptor, wherein the human 5-HT$_{1D}$ receptor is a human 5-HT$_{1D-1}$ receptor and a human 5-HT$_{1D-2}$ receptor, so as to treat the subject's migraine with the proviso that the compound is not methylergonovine, ergotamine, sumatriptan or pindolol.

7. A pharmaceutical composition for treating migraine in a subject which comprises an acceptable carrier and an amount of a chemical compound which selectively binds to and activates a human 5-HT$_{1D-1}$ receptor and a human 5-HT$_{1D-2}$ receptor but not a 5-HT$_{1A}$ receptor, a 5-HT$_{1E}$ receptor, a 5-HT$_2$ receptor, a 5-HT$_3$ receptor, or a 5-HT$_4$ receptor effective to treat the subject's migraine with the proviso that the compound is not methylergonovine, ergotamine, sumatriptan or pindolol.

8. A pharmaceutical composition for treating migraine in a subject which comprises an acceptable carrier and an amount of a chemical compound which selectively binds to and activates a human 5-HT$_{1D-1}$ receptor and a human 5-HT$_{1D-2}$ receptor but not any other serotonin receptor effective to treat the subject's migraine with the proviso that the compound is not methylergonovine, ergotamine, sumatriptan or pindolol.

* * * * *

UNITED STATES PATENT AND TRADEMARK OFFICE
CERTIFICATE OF CORRECTION

PATENT NO. : 5,935,925
DATED : August 10, 1999
INVENTOR(S) : Richard L. Weinshank et al.

It is certified that error appears in the above-identified patent and that said Letters Patent is hereby corrected as shown below:

Column 5,
Line 61, change "Hind III-SphI-dog" to -- Hind III-Sph I -- dog --
Line 67, change "5-HT$_{1D-1}$ (Sequence I.D. Nos. 1 and 2)" to -- 5-HT$_{1D-1}$ (gene 8-30-84) (Sequence I.D. Nos. 1 and 2) --

Column 6,
Line 17, change "5-HT$_{1D-2}$ (Sequence I.D. Nos. 3 and 4)" to -- 5-HT$_{1D-2}$ (gene 11) (Sequence I.D. Nos. 3 and 4) --

Column 19,
Line 25, change "5-HT$_{1E}$" to -- 5-HT$_{1B}$ --
Line 39, change "Titler" to -- Titeler --

Column 22,
Line 53, change "compression" to -- comparison --
Line 29, change "doe" to -- does --

Column 24,
Line 15, change "psuedotransfected" to -- pseudotransfected --
Line 29, change "8   -30-84" to -- 8-30-84 --
Line 30, change "K" to -- K$_d$ --

Column 25,
Table 1, "Tryptamine 521 $\pm$ 32 340$^b$" should read -- Tryptamine 521 $\pm$ 82 46$^c$ --
Table 1, "mCPP 429 $\pm$ 80" should read -- mCPP 329 $\pm$ 80 --
Line 38, "clone" should read -- cloned --

UNITED STATES PATENT AND TRADEMARK OFFICE
CERTIFICATE OF CORRECTION

PATENT NO.    : 5,935,925
DATED         : August 10, 1999
INVENTOR(S)   : Richard L. Weinshank et al.

It is certified that error appears in the above-identified patent and that said Letters Patent is hereby corrected as shown below:

Column 26,
Line 36, "5-HT$_{1A}$, 5-HT$_{1B}$, 5-HT$_{1C}$, 5-HT$_3$, or 5-HT$_4$," should read -- 5-HT$_{1A}$, 5-HT$_{1B}$, 5-HT$_{1C}$, 5-HT$_2$, 5-HT$_3$, or 5-HT$_4$, --

Column 39,
Line 6, "5-HT2" should read -- 5-HT$_2$ --

Signed and Sealed this

Eleventh Day of December, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1645 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 284..1414

(xi) SEQUENCE DESCRIPTION: SEQ ID NO:1:

```
TGTGGTTTAG GAAAGACCTT TAACTACCAG CTGGTAGTTG TCTCAGCATT CTTCAAATAG      60

TCCGGTCTTG TTTAATAATA TTATTATTAT TGTTATTTAA TTTTATTTTA TTGCAACTGT     120

ACTTAGAGAA TAGTCTGGTC TTGAGACCTT TTCACTGTGG TCTGTTCTGG TGTACGGCTC     180

CCACCAGTGT GAAGCAGAAG GATGACTTTG CTCTGTTGTC AGGACAACCT TGAAGGAAGG     240

AGCCAAATGT GTGGAGGTCT GTGGGAAGAG AGAGCCACCT AGC ATG TCC CCA CTG      295
                                                Met Ser Pro Leu
                                                  1

AAC CAG TCA GCA GAA GGC CTT CCC CAG GAG GCC TCC AAC AGA TCC CTG      343
Asn Gln Ser Ala Glu Gly Leu Pro Gln Glu Ala Ser Asn Arg Ser Leu
  5                  10                  15                  20

AAT GCC ACA GAA ACC TCA GAG GCT TGG GAT CCC AGG ACC CTC CAG GCG      391
Asn Ala Thr Glu Thr Ser Glu Ala Trp Asp Pro Arg Thr Leu Gln Ala
                 25                  30                  35

CTC AAG ATC TCC CTT GCC GTG GTC CTT TCC GTC ATC ACA CTG GCC ACA      439
Leu Lys Ile Ser Leu Ala Val Val Leu Ser Val Ile Thr Leu Ala Thr
```

-continued

```
                     40                  45                  50
GTC CTC TCC AAT GCC TTT GTA CTC ACC ACC ATC TTA CTC ACC AGG AAG       487
Val Leu Ser Asn Ala Phe Val Leu Thr Thr Ile Leu Leu Thr Arg Lys
             55                  60                  65

CTC CAC ACC CCT GCC AAC TAC CTG ATT GGC TCC CTG GCC ACC ACC GAC       535
Leu His Thr Pro Ala Asn Tyr Leu Ile Gly Ser Leu Ala Thr Thr Asp
         70                  75                  80

CTC TTG GTT TCC ATC TTG GTA ATG CCC ATC AGC ATC GCC TAT ACC ATC       583
Leu Leu Val Ser Ile Leu Val Met Pro Ile Ser Ile Ala Tyr Thr Ile
 85                  90                  95                 100

ACC CAC ACC TGG AAC TTT GGC CAA ATC TTG TGT GAC ATC TGG CTG TCC       631
Thr His Thr Trp Asn Phe Gly Gln Ile Leu Cys Asp Ile Trp Leu Ser
                         105                 110                 115

TCT GAC ATC ACG TGC TGC ACA GCC TCC ATC CTG CAT CTC TGT GTC ATT       679
Ser Asp Ile Thr Cys Cys Thr Ala Ser Ile Leu His Leu Cys Val Ile
             120                 125                 130

GCT CTG GAC AGG TAC TGG GCA ATC ACA GAT GCC CTG GAA TAC AGT AAA       727
Ala Leu Asp Arg Tyr Trp Ala Ile Thr Asp Ala Leu Glu Tyr Ser Lys
         135                 140                 145

CGC AGG ACG GCT GGC CAC GCG GCC ACC ATG ATC GCC ATT GTC TGG GCC       775
Arg Arg Thr Ala Gly His Ala Ala Thr Met Ile Ala Ile Val Trp Ala
 150                 155                 160

ATC TCC ATC TGC ATC TCC ATC CCC CCG CTC TTC TGG CGG CAG GCC AAG       823
Ile Ser Ile Cys Ile Ser Ile Pro Pro Leu Phe Trp Arg Gln Ala Lys
165                 170                 175                 180

GCC CAG GAG GAG ATG TCG GAC TGT CTG GTG AAC ACC TCT CAG ATC TCC       871
Ala Gln Glu Glu Met Ser Asp Cys Leu Val Asn Thr Ser Gln Ile Ser
                     185                 190                 195

TAC ACC ATC TAC TCC ACC TGT GGG GCC TTC TAC ATT CCC TCG GTG TTG       919
Tyr Thr Ile Tyr Ser Thr Cys Gly Ala Phe Tyr Ile Pro Ser Val Leu
             200                 205                 210

CTC ATC ATC CTA TAT GGC CGG ATC TAC CGG GCT GCC CGG AAC CGC ATC       967
Leu Ile Ile Leu Tyr Gly Arg Ile Tyr Arg Ala Ala Arg Asn Arg Ile
         215                 220                 225

CTG AAT CCA CCC TCA CTC TAT GGG AAG CGC TTC ACC ACG GCC CAC CTC      1015
Leu Asn Pro Pro Ser Leu Tyr Gly Lys Arg Phe Thr Thr Ala His Leu
 230                 235                 240

ATC ACA GGC TCT GCC GGG TCC TCG CTC TGC TCG CTC AAC TCC AGC CTC      1063
Ile Thr Gly Ser Ala Gly Ser Ser Leu Cys Ser Leu Asn Ser Ser Leu
245                 250                 255                 260

CAT GAG GGG CAC TCG CAC TCG GCT GGC TCC CCT CTC TTT TTC AAC CAC      1111
His Glu Gly His Ser His Ser Ala Gly Ser Pro Leu Phe Phe Asn His
                     265                 270                 275

GTG AAA ATC AAG CTT GCT GAC AGT GCC CTG GAA CGC AAG AGG ATT TCT      1159
Val Lys Ile Lys Leu Ala Asp Ser Ala Leu Glu Arg Lys Arg Ile Ser
             280                 285                 290

GCT GCT CGA GAA AGG AAA GCC ACT AAA ATC CTG GGC ATC ATT CTG GGG      1207
Ala Ala Arg Glu Arg Lys Ala Thr Lys Ile Leu Gly Ile Ile Leu Gly
         295                 300                 305

GCC TTT ATC ATC TGC TGG CTG CCC TTC TTC GTG GTG TCT CTG GTC CTC      1255
Ala Phe Ile Ile Cys Trp Leu Pro Phe Phe Val Val Ser Leu Val Leu
 310                 315                 320

CCC ATC TGC CGG GAC TCC TGC TGG ATC CAC CCG GCG CTC TTT GAC TTC      1303
Pro Ile Cys Arg Asp Ser Cys Trp Ile His Pro Ala Leu Phe Asp Phe
325                 330                 335                 340

TTC ACC TGG CTA GGC TAT TTA AAC TCC CTC ATC AAT CCA ATA ATC TAC      1351
Phe Thr Trp Leu Gly Tyr Leu Asn Ser Leu Ile Asn Pro Ile Ile Tyr
                     345                 350                 355

ACT GTG TTT AAT GAA GAG TTT CGG CAA GCT TTT CAG AAA ATT GTC CCT      1399
Thr Val Phe Asn Glu Glu Phe Arg Gln Ala Phe Gln Lys Ile Val Pro
```

```
                    360                 365                 370
TTC CGG AAG GCC TCC TAGTCTTATT CGATGAGGTA AAGAAACCTG CTTATGGGCT      1454
Phe Arg Lys Ala Ser
        375

GGGCATGGTG GCTCATGCCT GTGATCCCAG CACTTTGGGA AGCTGAAGAG GAGGACTACT    1514

TGAGCTCAGG AGTTTGAGAC CAGCCTGGGC AGCATAGGGA GACCCCGTCT CTAACGACAA    1574

CAACAGAAAT TACCGGACAT GGTGGAGCGC GCCAGTAGTC CCAGCTACTC GAGAGGCTGT    1634

GGCTACAGTG A                                                        1645

(2) INFORMATION FOR SEQ ID NO:2:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Pro Leu Asn Gln Ser Ala Glu Gly Leu Pro Gln Glu Ala Ser
 1               5                  10                  15

Asn Arg Ser Leu Asn Ala Thr Glu Thr Ser Glu Ala Trp Asp Pro Arg
            20                  25                  30

Thr Leu Gln Ala Leu Lys Ile Ser Leu Ala Val Val Leu Ser Val Ile
        35                  40                  45

Thr Leu Ala Thr Val Leu Ser Asn Ala Phe Val Leu Thr Thr Ile Leu
    50                  55                  60

Leu Thr Arg Lys Leu His Thr Pro Ala Asn Tyr Leu Ile Gly Ser Leu
65                  70                  75                  80

Ala Thr Thr Asp Leu Leu Val Ser Ile Leu Val Met Pro Ile Ser Ile
                85                  90                  95

Ala Tyr Thr Ile Thr His Thr Trp Asn Phe Gly Gln Ile Leu Cys Asp
            100                 105                 110

Ile Trp Leu Ser Ser Asp Ile Thr Cys Cys Thr Ala Ser Ile Leu His
        115                 120                 125

Leu Cys Val Ile Ala Leu Asp Arg Tyr Trp Ala Ile Thr Asp Ala Leu
    130                 135                 140

Glu Tyr Ser Lys Arg Arg Thr Ala Gly His Ala Ala Thr Met Ile Ala
145                 150                 155                 160

Ile Val Trp Ala Ile Ser Ile Cys Ile Ser Ile Pro Pro Leu Phe Trp
                165                 170                 175

Arg Gln Ala Lys Ala Gln Glu Glu Met Ser Asp Cys Leu Val Asn Thr
            180                 185                 190

Ser Gln Ile Ser Tyr Thr Ile Tyr Ser Thr Cys Gly Ala Phe Tyr Ile
        195                 200                 205

Pro Ser Val Leu Leu Ile Ile Leu Tyr Gly Arg Ile Tyr Arg Ala Ala
    210                 215                 220

Arg Asn Arg Ile Leu Asn Pro Pro Ser Leu Tyr Gly Lys Arg Phe Thr
225                 230                 235                 240

Thr Ala His Leu Ile Thr Gly Ser Ala Gly Ser Ser Leu Cys Ser Leu
                245                 250                 255

Asn Ser Ser Leu His Glu Gly His Ser His Ser Ala Gly Ser Pro Leu
            260                 265                 270

Phe Phe Asn His Val Lys Ile Lys Leu Ala Asp Ser Ala Leu Glu Arg
        275                 280                 285
```

```
Lys Arg Ile Ser Ala Ala Arg Glu Arg Lys Ala Thr Lys Ile Leu Gly
    290                 295                 300

Ile Ile Leu Gly Ala Phe Ile Ile Cys Trp Leu Pro Phe Phe Val Val
305                 310                 315                 320

Ser Leu Val Leu Pro Ile Cys Arg Asp Ser Cys Trp Ile His Pro Ala
                325                 330                 335

Leu Phe Asp Phe Phe Thr Trp Leu Gly Tyr Leu Asn Ser Leu Ile Asn
            340                 345                 350

Pro Ile Ile Tyr Thr Val Phe Asn Glu Glu Phe Arg Gln Ala Phe Gln
        355                 360                 365

Lys Ile Val Pro Phe Arg Lys Ala Ser
    370                 375
```

(2) INFORMATION FOR SEQ ID NO:3:

(i) SEQUENCE CHARACTERISTICS:
        (A) LENGTH: 1690 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 122..1291

(xi) SEQUENCE DESCRIPTION: SEQ ID NO:3:

```
ATTGAGGAAC TCACGGAACT ATCAACTGGG AACAAACCTG CGATCGCCAC GGTCCTTCCG    60

CCCTCTCCTT CGTCCGCTCC ATGCCCAAGA GCTGCGCTCC GGAGCTGGGG CGAGGAGAGC   120

C ATG GAG GAA CCG GGT GCT CAG TGC GCT CCA CCG CCG CCC GCG GGC       166
  Met Glu Glu Pro Gly Ala Gln Cys Ala Pro Pro Pro Pro Ala Gly
      380                 385                 390

TCC GAG ACC TGG GTT CCT CAA GCC AAC TTA TCC TCT GCT CCC TCC CAA     214
Ser Glu Thr Trp Val Pro Gln Ala Asn Leu Ser Ser Ala Pro Ser Gln
            395                 400                 405

AAC TGC AGC GCC AAG GAC TAC ATT TAC CAG GAC TCC ATC TCC CTA CCC     262
Asn Cys Ser Ala Lys Asp Tyr Ile Tyr Gln Asp Ser Ile Ser Leu Pro
    410                 415                 420

TGG AAA GTA CTG CTG GTT ATG CTA TTG GCG CTC ATC ACC TTG GCC ACC     310
Trp Lys Val Leu Leu Val Met Leu Leu Ala Leu Ile Thr Leu Ala Thr
425                 430                 435                 440

ACG CTC TCC AAT GCC TTT GTG ATT GCC ACA GTG TAC CGG ACC CGG AAA     358
Thr Leu Ser Asn Ala Phe Val Ile Ala Thr Val Tyr Arg Thr Arg Lys
                445                 450                 455

CTG CAC ACC CCG GCT AAC TAC CTG ATC GCC TCT CTG GCA GTC ACC GAC     406
Leu His Thr Pro Ala Asn Tyr Leu Ile Ala Ser Leu Ala Val Thr Asp
            460                 465                 470

CTG CTT GTG TCC ATC CTG GTG ATG CCC ATC AGC ACC ATG TAC ACT GTC     454
Leu Leu Val Ser Ile Leu Val Met Pro Ile Ser Thr Met Tyr Thr Val
        475                 480                 485

ACC GGC CGC TGG ACA CTG GGC CAG GTG GTC TGT GAC TTC TGG CTG TCG     502
Thr Gly Arg Trp Thr Leu Gly Gln Val Val Cys Asp Phe Trp Leu Ser
    490                 495                 500

TCG GAC ATC ACT TGT TGC ACT GCC TCC ATC CTG CAC CTC TGT GTC ATC     550
Ser Asp Ile Thr Cys Cys Thr Ala Ser Ile Leu His Leu Cys Val Ile
505                 510                 515                 520

GCC CTG GAC CGC TAC TGG GCC ATC ACG GAC GCC GTG GAG TAC TCA GCT     598
Ala Leu Asp Arg Tyr Trp Ala Ile Thr Asp Ala Val Glu Tyr Ser Ala
                525                 530                 535

AAA AGG ACT CCC AAG AGG GCG GCG GTC ATG ATC GCG CTG GTG TGG GTC     646
```

```
Lys Arg Thr Pro Lys Arg Ala Ala Val Met Ile Ala Leu Val Trp Val
        540                 545                 550

TTC TCC ATC TCT ATC TCG CTG CCG CCC TTC TTC TGG CGT CAG GCT AAG         694
Phe Ser Ile Ser Ile Ser Leu Pro Pro Phe Phe Trp Arg Gln Ala Lys
            555                 560                 565

GCC GAA GAG GAG GTG TCG GAA TGC GTG GTG AAC ACC GAC CAC ATC CTC         742
Ala Glu Glu Glu Val Ser Glu Cys Val Val Asn Thr Asp His Ile Leu
    570                 575                 580

TAC ACG GTC TAC TCC ACG GTG GGT GCT TTC TAC TTC CCC ACC CTG CTC         790
Tyr Thr Val Tyr Ser Thr Val Gly Ala Phe Tyr Phe Pro Thr Leu Leu
585                 590                 595                 600

CTC ATC GCC CTC TAT GGC CGC ATC TAC GTA GAA GCC CGC TCC CGG ATT         838
Leu Ile Ala Leu Tyr Gly Arg Ile Tyr Val Glu Ala Arg Ser Arg Ile
                605                 610                 615

TTG AAA CAG ACG CCC AAC AGG ACC GGC AAG CGC TTG ACC CGA GCC CAG         886
Leu Lys Gln Thr Pro Asn Arg Thr Gly Lys Arg Leu Thr Arg Ala Gln
            620                 625                 630

CTG ATA ACC GAC TCC CCC GGG TCC ACG TCC TCG GTC ACC TCT ATT AAC         934
Leu Ile Thr Asp Ser Pro Gly Ser Thr Ser Ser Val Thr Ser Ile Asn
    635                 640                 645

TCG CGG GTT CCC GAC GTG CCC AGC GAA TCC GGA TCT CCT GTG TAT GTG         982
Ser Arg Val Pro Asp Val Pro Ser Glu Ser Gly Ser Pro Val Tyr Val
650                 655                 660

AAC CAA GTC AAA GTG CGA GTC TCC GAC GCC CTG CTG GAA AAG AAG AAA        1030
Asn Gln Val Lys Val Arg Val Ser Asp Ala Leu Leu Glu Lys Lys Lys
665                 670                 675                 680

CTC ATG GCC GCT AGG GAG CGC AAA GCC ACC AAG ACC CTA GGG ATC ATT        1078
Leu Met Ala Ala Arg Glu Arg Lys Ala Thr Lys Thr Leu Gly Ile Ile
            685                 690                 695

TTG GGA GCC TTT ATT GTG TGT TGG CTA CCC TTC TTC ATC ATC TCC CTA        1126
Leu Gly Ala Phe Ile Val Cys Trp Leu Pro Phe Phe Ile Ile Ser Leu
    700                 705                 710

GTG ATG CCT ATC TGC AAA GAT GCC TGC TGG TTC CAC CTA GCC ATC TTT        1174
Val Met Pro Ile Cys Lys Asp Ala Cys Trp Phe His Leu Ala Ile Phe
715                 720                 725

GAC TTC TTC ACA TGG CTG GGC TAT CTC AAC TCC CTC ATC AAC CCC ATA        1222
Asp Phe Phe Thr Trp Leu Gly Tyr Leu Asn Ser Leu Ile Asn Pro Ile
            730                 735                 740

ATC TAT ACC ATG TCC AAT GAG GAC TTT AAA CAA GCA TTC CAT AAA CTG        1270
Ile Tyr Thr Met Ser Asn Glu Asp Phe Lys Gln Ala Phe His Lys Leu
745                 750                 755                 760

ATA CGT TTT AAG TGC ACA AGT TGACTTGCCG TTTGCAGTGG GGTCGCCTAA           1321
Ile Arg Phe Lys Cys Thr Ser
                765

GCGACCTTTG GGACCAAGT TGTGTCTGGT TCCACAGGTA GGTCGAATCT TCTTTCGCGG       1381

TTTCTGGGTC CCAGCGAGGC TCTCTCTCCT GGGCAAGGGC AATGGATCCT GAGAAGCCAG      1441

AATAGTCCTG AGAGAGAGCT CTGAAAGGAG AAGTGTTGAA ACTAAATGTA GAGCTTCCCT      1501

GCCCAGGAGG AGGCTCACTT CCTCCCCTCA AGCCCCGGGC TCAGCACTGA CCTGCGGCAG      1561

CCAATCCAAG GGGGTTGCAA CTTTTAAAAA TTGATATGGA AGGGAATCCC TGCCCTGCTT      1621

TGGTATCGTG ATAATGCCCA CTAGAAGCAG TGTACTGTAA TTGTTGTCTG AAGCCTGTCT      1681

GAGACAGAT                                                              1690

(2) INFORMATION FOR SEQ ID NO:4:

(i) SEQUENCE CHARACTERISTICS:
        (A) LENGTH: 390 amino acids
        (B) TYPE: amino acid
        (D) TOPOLOGY: linear
```

(ii) MOLECULE TYPE: protein (xi) SEQUENCE DESCRIPTION: SEQ ID NO:4:

| Met | Glu | Glu | Pro | Gly | Ala | Gln | Cys | Ala | Pro | Pro | Pro | Ala | Gly | Ser |
|---|---|---|---|---|---|---|---|---|---|---|---|---|---|---|
| 1 | | | | 5 | | | | | 10 | | | | | 15 |

| Glu | Thr | Trp | Val | Pro | Gln | Ala | Asn | Leu | Ser | Ser | Ala | Pro | Ser | Gln | Asn |
|---|---|---|---|---|---|---|---|---|---|---|---|---|---|---|---|
| | | | 20 | | | | | 25 | | | | | 30 | | |

Cys Ser Ala Lys Asp Tyr Ile Tyr Gln Asp Ser Ile Ser Leu Pro Trp
            35                  40                  45

Lys Val Leu Leu Val Met Leu Leu Ala Leu Ile Thr Leu Ala Thr Thr
50                      55                      60

Leu Ser Asn Ala Phe Val Ile Ala Thr Val Tyr Arg Thr Arg Lys Leu
65                      70                      75              80

His Thr Pro Ala Asn Tyr Leu Ile Ala Ser Leu Ala Val Thr Asp Leu
                85                  90                  95

Leu Val Ser Ile Leu Val Met Pro Ile Ser Thr Met Tyr Thr Val Thr
                100                 105                 110

Gly Arg Trp Thr Leu Gly Gln Val Val Cys Asp Phe Trp Leu Ser Ser
            115                 120                 125

Asp Ile Thr Cys Cys Thr Ala Ser Ile Leu His Leu Cys Val Ile Ala
130                 135                 140

Leu Asp Arg Tyr Trp Ala Ile Thr Asp Ala Val Glu Tyr Ser Ala Lys
145                 150                 155                 160

Arg Thr Pro Lys Arg Ala Ala Val Met Ile Ala Leu Val Trp Val Phe
                165                 170                 175

Ser Ile Ser Ile Ser Leu Pro Pro Phe Phe Trp Arg Gln Ala Lys Ala
            180                 185                 190

Glu Glu Glu Val Ser Glu Cys Val Val Asn Thr Asp His Ile Leu Tyr
                195                 200                 205

Thr Val Tyr Ser Thr Val Gly Ala Phe Tyr Phe Pro Thr Leu Leu Leu
210                 215                 220

Ile Ala Leu Tyr Gly Arg Ile Tyr Val Glu Ala Arg Ser Arg Ile Leu
225                 230                 235                 240

Lys Gln Thr Pro Asn Arg Thr Gly Lys Arg Leu Thr Arg Ala Gln Leu
                245                 250                 255

Ile Thr Asp Ser Pro Gly Ser Thr Ser Ser Val Thr Ser Ile Asn Ser
            260                 265                 270

Arg Val Pro Asp Val Pro Ser Glu Ser Gly Ser Pro Val Tyr Val Asn
                275                 280                 285

Gln Val Lys Val Arg Val Ser Asp Ala Leu Leu Glu Lys Lys Lys Leu
            290                 295                 300

Met Ala Ala Arg Glu Arg Lys Ala Thr Lys Thr Leu Gly Ile Ile Leu
305                 310                 315                 320

Gly Ala Phe Ile Val Cys Trp Leu Pro Phe Phe Ile Ile Ser Leu Val
                325                 330                 335

Met Pro Ile Cys Lys Asp Ala Cys Trp Phe His Leu Ala Ile Phe Asp
                340                 345                 350

Phe Phe Thr Trp Leu Gly Tyr Leu Asn Ser Leu Ile Asn Pro Ile Ile
            355                 360                 365

Tyr Thr Met Ser Asn Glu Asp Phe Lys Gln Ala Phe His Lys Leu Ile
370                 375                 380

Arg Phe Lys Cys Thr Ser
385                 390